US006838428B2

(12) United States Patent
Whitsett

(10) Patent No.: US 6,838,428 B2
(45) Date of Patent: Jan. 4, 2005

(54) SURFACTANT PROTEIN D FOR THE PREVENTION AND DIAGNOSIS OF PULMONARY EMPHYSEMA

(75) Inventor: Jeffrey A. Whitsett, Cincinnati, OH (US)

(73) Assignee: Children's Hospital Medical Center, Cincinnatti, OH (US)

( * ) Notice: Subject to any disclaimer, the term of this patent is extended or adjusted under 35 U.S.C. 154(b) by 180 days.

(21) Appl. No.: 09/558,576

(22) Filed: Apr. 26, 2000

(65) Prior Publication Data

US 2003/0172389 A1 Sep. 11, 2003

Related U.S. Application Data

(63) Continuation-in-part of application No. PCT/US99/24675, filed on Oct. 20, 1999.
(60) Provisional application No. 60/104,941, filed on Oct. 20, 1998.

(51) Int. Cl.$^7$ .......................... A61K 38/00; A61K 35/42
(52) U.S. Cl. ................................ 514/2; 514/12; 514/14; 514/13; 514/888; 424/557; 435/69.1; 435/69.7
(58) Field of Search ................................ 514/2, 12, 14, 514/13; 424/557; 435/69.1, 69.7

(56) References Cited

U.S. PATENT DOCUMENTS

| 5,670,328 A | * | 9/1997 | Inoue et al. ................ 435/7.23 |
| 6,013,619 A | * | 1/2000 | Cochrane et al. .............. 514/2 |
| 6,046,158 A | * | 4/2000 | Ariizumi et al. ................ 514/2 |
| 6,180,142 B1 | * | 1/2001 | Taeusch ....................... 424/557 |

FOREIGN PATENT DOCUMENTS

| WO | WO 94/23582 | 10/1994 |
| WO | WO 00/23569 | 4/2000 |

OTHER PUBLICATIONS

Johansson et al. The proteins of the surfactant system, 1994, Eur. Respir. J. 7: 372–391.*
Jobe et al. Surfactant for the Treatment of Respiratory Distress Syndrome, 1987, Am. Rev. Respir. Dis. 136: 1256–1275.*
McCormack, Molecular Biology of the Surfactant Apoproteins, Jan. 1995, Sem. Respir, Crit. Med. 16(1): 29–38.*
Lu et al. Purification, characterization and cDNA cloning of human lung surfactant protein D. (1992) Biochem. J. 284: 795–802.*
Hickling et al. A recombinant trimeric surfactant protein D carboydrate recognition domain inhibits respiratory syncytial virus infections in vitro and in vivo. (1999) Eur. J. Immunol. 29: 3478–3484.*
Borron et al. Recombinant rat surfactant–associated protein D inhibits human T lymphocyte proliferation and IL–2 production. Nov. 1998, J. Immunol. 161: 4599–4603.*
Reid, K.B.M. Functional role of lung surfactant proteins SP–A and SP–D in innate immunity. 1998, Immunobiol. 199: 200–207.*
Shimizu, et al. *Primary Structure of Rat Pulmonary Surfactant Protein D*, The Journal of Biological Chemistry, vol. 267, No. 3, Jan. 25, pp. 1853–1857 (1992).
Crouch, Erika C., "Surfactant protein–D and pulmonary host defense", *Respiratory Research*, 1:93–108, (2000).
Fisher, et al., "Pulmonary–specific expression of SP–D corrects pulmonary lipid accumulation in SP–D gene–targeted mice", *Am. J. Physiol. Lung Cell. Mol Physiol.* 278:L365–L373, (2000).
Hartshorn, et al., "Evidence for a Protective Role of Pulmonary Surfactant Protein D (SP–D) against Influenza A Viruses",*J. Clin. Invest.* The American Society for Clinical Investigation, Inc. 94:311–319, (1994).
Botas, et al. "Altered surfactant homeostasis and alveolar type II cell morphology in mice lacking surfactant protein D" *Proc. Natl. Acad. Sci. USA* vol. 95, pp. 11869–11874, Sep. 1998.
Shilpa Jain–Vora et al., *Interleukin–4 Enhances Pulmonary Clearance of Pseudomonas aeruginosa, Infection and Immunity*, vol. 66, No. 9, Sep. 1998, pp. 4229–4236.
Shih–Fan Kuan et al., *Interactions of Surfactant Protein D with Bacterial Lipopolysaccharides, J. Clin. Invest.*, vol. 90, Jul. 1992, pp. 97–106.
Edmond Crouch et al., *Genomic Organization of Human Surfactant Protein D (SP–D)*, The Journal of Biological Chemistry, vol. 268, No. 4., Feb. 5, 1993, pp. 2976–2983.
S.M. Singh et al., *Strategies and application of DNA level diagnosis in genetic diseases: past experiences and future directions, Biotechnology Annual Review*, vol. 2, 1996, pp. 409–446.
Richard C. Mulligan, *The Basic Science of Gene Therapy*, Science, vol. 260, May 14, 1993, pp. 926–932.
Thomas R. Korfhagen et al.,*Altered surfactant function and structure in SP–A gene targeted mice*, Proc. Natl. Acad. Sci. USA, vol. 93, Sep. 1996, pp. 9594–9599.
Ann Marie LeVine et al., *Surfactant Protein A–Deficient Mice Are Susceptible to Group B Streptococcal Infection*, The Journal of Immunology, 1997, pp. 4336–4340.

* cited by examiner

Primary Examiner—Christopher S. F. Low
Assistant Examiner—Holly Schnizer
(74) Attorney, Agent, or Firm—Knobbe, Martens, Olson & Bear, LLP

(57) ABSTRACT

Surfactant protein D (SP-D) is a 43-kDa member of the collectin family of collagenous lectin domain-containing proteins that is expressed in epithelial cells of the lung. The SP-D gene was targeted by homologous recombination in embryonic stem cells that were used to produce SP-D (–/–) mice. The SP-D (–/–) deficiency caused inflammation, increased oxidant production by isolated alveolar macrophages, abnormal surfactant structure and levels, and decreased SP-A expression. Therefore, disclosed is the SP-D (–/–) mouse as an excellent model for emphysema. Also included are models for testing emphysema therapies in the mouse model, methods for using SP-D protein or DNA as a treatment for emphysema and pulmonary infections, and diagnosis.

27 Claims, 18 Drawing Sheets

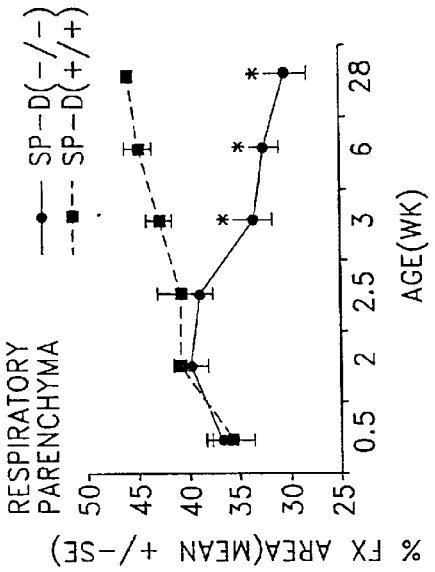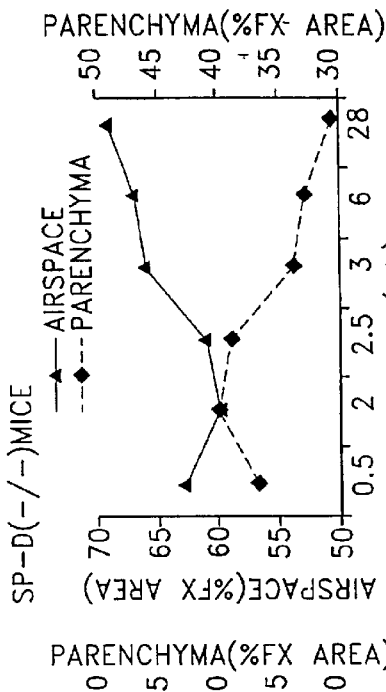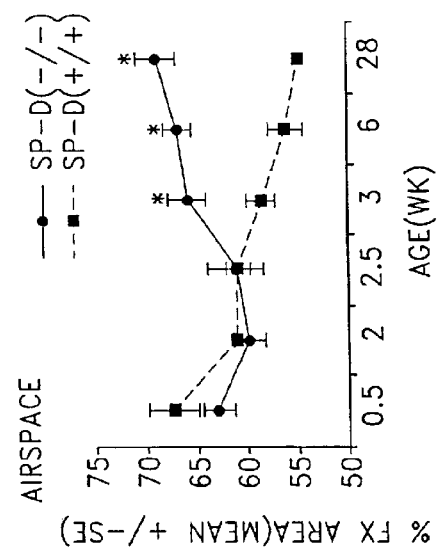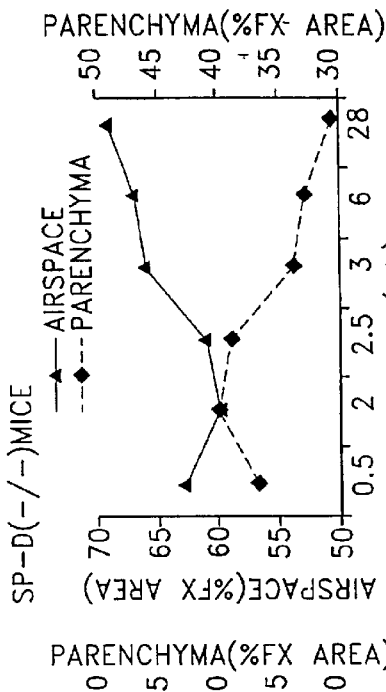

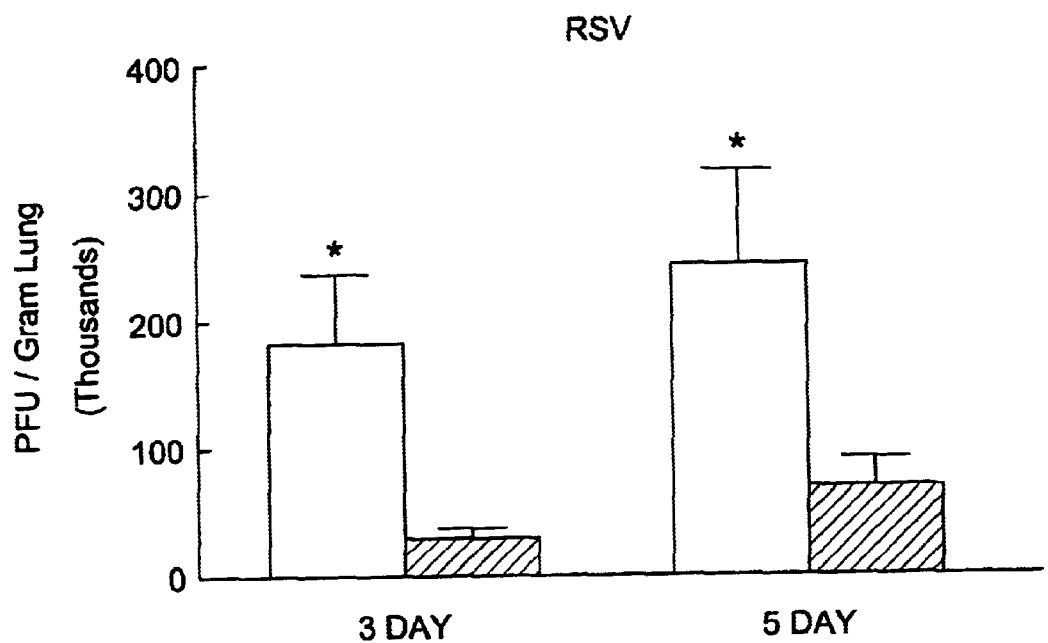
*FIG. 16A*
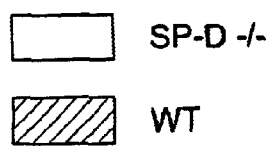
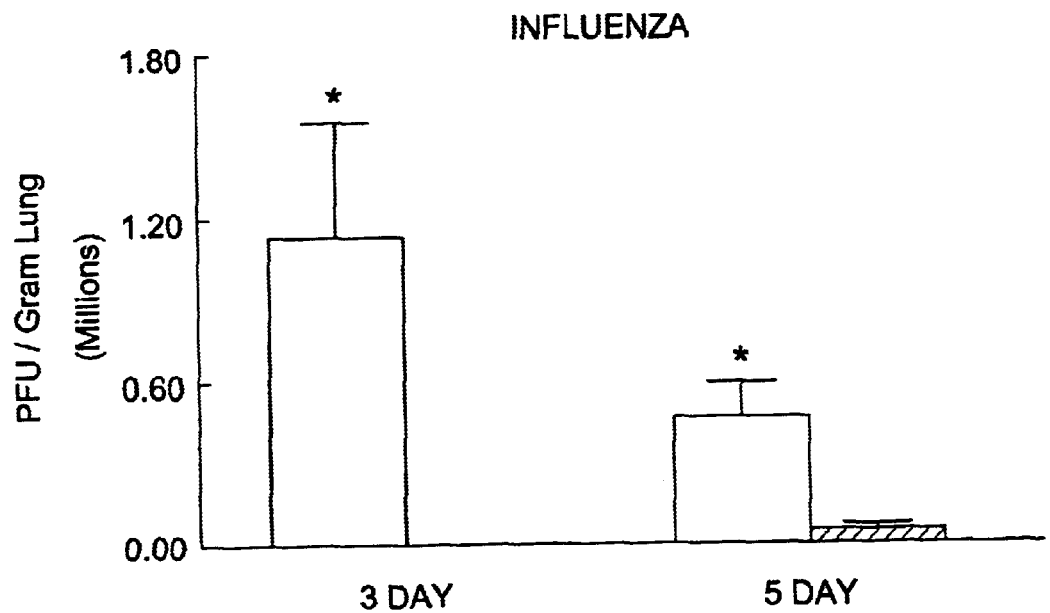
*FIG. 16B*

SURFACTANT PROTEIN D FOR THE PREVENTION AND DIAGNOSIS OF PULMONARY EMPHYSEMA

This application is a Continuation in Part of PCT/US99/24675, filed Oct. 20, 1999 which claims priority under 35 U.S.C. 119(e) of U.S. Provisional application No. 60/104,941, filing date Oct. 20, 1998.

GOVERNMENT INTEREST IN THE INVENTION

Certain aspects of the invention disclosed herein were made with United States government support under National Institutes of Health grants HL 41320, SCOR HL 56387, HL 28623, HL 58795, and HL03905. The United States government has certain rights in these aspects of the invention.

FIELD OF THE INVENTION

The present invention relates generally to the field of biologically active proteins. More specifically the present invention relates to SP-D proteins involved in pulmonary surfactant homeostasis and structure, and alveolar structure in the lungs and SP-D (−/−) null mice.

BACKGROUND OF THE INVENTION

Pulmonary surfactant is essential for normal lung mechanics and gas exchange in the lung. Pulmonary surfactant is produced by type II epithelial cells and is made up of a phospholipid component which confers the ability of surfactant to lower surface tension in the lung. In addition, there are proteins associated with the surfactant called collectins which are collagenous, lectin domain-containing polypeptides. Two of these, designated surfactant protein A (SP-A) and surfactant protein D (SP-D), are likely involved in surfactant structure and function and host defense. Both quantitative and qualitative deficiencies in pulmonary surfactant are associated with neonatal respiratory distress, adult respiratory distress syndrome, congenital deficiencies of surfactant protein B, and allergic asthma. In addition, deficiency in pulmonary surfactant may contribute to the increased susceptibility of some individuals to microbial challenge, especially in the setting of inadequate or impaired specific immunity. These disorders as well as some disorders associated with increased risk of pneumonia (cystic fibrosis, asthma, prematurity, chronic bronchitis, diffuse alveolar damage) may also be associated with acquired defects or deficiency in collectin function. Alveolar surfactant pools are regulated at multiple levels including intracellular synthesis, secretion, re-uptake and degradation of these components by alveolar macrophages. The synthesis and clearance of surfactant phospholipids and proteins is further influenced by developmental, mechanical, and humoral stimuli that serve to maintain steady-state surfactant concentrations after birth.

The role of the collectins in surfactant and normal lung function has been extensively investigated. The collectin family of C-type lectins includes a number of molecules with known host defense functions. SP-A and SP-D, also C-type lectins, bind influenza and herpes simplex viruses as well as gram positive and gram-negative bacteria and various fungi. By binding they enhance uptake by alveolar macrophages and neutrophils. Various cellular binding sites for SP-A and SP-D have been identified on alveolar macrophages or, in the case of SP-A, on type II epithelial cells. The critical role of SP-A in host defense was supported by the observation that SP-A-deficient mice are susceptible to infections by group B streptococcus, *Pseudomonas aeruginosa*, Respiratory syncytial virus, adenovirus, and mycoplasma in vivo. Thus, there is a clear role for SP-A and a likely role for SP-D in respiratory defense mechanisms. Collectins may also participate in the recognition or clearance of other complex organic materials, such as pollens and dust mite allergens. However, to date no human diseases have been associated with specific deficiencies in SP-A or SP-D.

SP-D is a 43 kilodalton protein that has been proposed to play a role in host defense in the lung. Its cDNA and gene have been sequenced in various mammals including humans. SP-D shares considerable structural homology with other C-type lectins, including surfactant protein A (SP-A), conglutinin, bovine collectin-43, and mannose binding protein. In vitro studies and its close structural relationship to a mammalian $Ca^{2+}$-dependent lectin family (particularly shared structural motifs) support its role in host defense. SP-D is synthesized primarily and at relatively high concentrations by Type II epithelial cells and nonciliated bronchiolar epithelial cells in the lung but may also be expressed in the gastrointestinal tract, heart, kidney, pancreas, genitourinary tract and mesentery cells. In vitro studies demonstrated that SP-D binds to the surface of organisms via its lectin domain (or sugar binding domain) which leads to binding, aggregation, opsonization and, in some instances, activation of killing by phagocytes in vitro. SP-D binds to lipopolysaccharide, various bacteria, fungi and viruses, including influenza virus. It also binds to both alveolar macrophages and polymorphonuclear cells. It may possibly play a role in surfactant phospholipid homeostasis, including the effects of SP-A on phospholipid metabolism by Type II cells in vitro, however, this is controversial and the precise role of SP-D in vivo is still unclear.

In vitro studies support the concept that surfactant proteins may be important in the regulation of surfactant homeostasis. Although the hydrophobic surfactant proteins SP-B and SP-C have roles in production of the surfactant monolayer, in vitro studies indicated that surfactant protein A may also facilitate surfactant uptake and/or secretion by type II epithelial cells. In fact, it was widely believed that SP-A would have a major role in surfactant homeostasis. However, recent studies of SP-A null mice have not supported the primary role of surfactant protein A in surfactant secretion or re-uptake. The absence of SP-A does not lead to obvious physiologic or morphologic structural abnormalities of the lung. SP-A null mutant mice lack tubular myelin figures but produce highly functional surfactant that absorbs rapidly and produces monolayers. Surfactant lipid synthesis, secretion, and re-uptake were essentially normal in SP-A null mice.

Therefore, the additional surfactant protein which acts in surfactant regulation is still not identified. In addition, the precise role of SP-D in normal lung function has not been clearly defined at this point and its role in disease or disease susceptibility is unclear.

SUMMARY OF THE INVENTION

The present invention provides an SP-D(−/−) mouse which can be used as a model for emphysema. Previously it was not known that SP-D protein was involved in lung lipid homeostasis. Nor was it known that an SP-D null mouse would have the symptoms of emphysema.

One embodiment of the invention is a non-human mammalian model for emphysema comprising an SP-D(−/−) non-human mammal.

A further embodiment is a method for the purification and treatment of pulmonary disease by introducing mammalian SP-D protein, or vectors expressing the mammalian SP-D protein into a human or mammal in an amount effective to reduce the symptoms of the disease or to prevent the disease.

A further embodiment is a pharmaceutical composition effective in treating pulmonary disease which is a mixture of SP-D protein with a pharmaceutically acceptable carrier.

A further embodiment is a biologically active agent for treating pulmonary disease in mammals which is an agent that up-regulates SP-D.

A further embodiment is a biologically active agent for treating pulmonary disease in mammals which is an agent that interacts with the SP-D protein.

A further embodiment is a method for diagnosing susceptibility to pulmonary disease in mammals by identifying a mutation in the SP-D gene which results in deficient SP-D, identifying that mutation in a test mammal by PCR, hybridization, or ELISA.

A further embodiment is a method of identifying pharmaceutical agents useful in treating pulmonary disease by allowing the SP-D null mouse to develop pulmonary disease, administering a pharmaceutical agent to the mammal, and identifying the agent as effective is the pulmonary disease improves.

A further embodiment is a method of purifying SP-D antibodies with a solid phase lung homogenate from any mouse which does not produce SP-D protein.

A further embodiment is a method for the prevention of pulmonary disease by introducing mammalian SP-D protein, or vectors expressing the mammalian SP-D protein into a human in an amount effective to reduce the symptoms of or prevent pulmonary disease, wherein the pulmonary disease is selected from the group consisting of: reactive oxygen-mediated disease, chemically induced lung injury, injury due to oxygen radicals, injury due to ozone, injury due to chemotherapeutic agents, inflammatory and infectious diseases, reperfusion injury, drowning, transplantation, and rejection.

A further embodiment of the invention is a method for the treatment of viral disease by introducing mammalian SP-D protein, or vectors expressing the mammalian SP-D protein into a human in an amount effective to reduce the number of viruses or symptoms of the viral disease. Preferably, the viruses are adenovirus, RSV, and Influenza virus.

BRIEF DESCRIPTION OF THE DRAWINGS

FIG. 1: Comparison of changes in fractional areas (% Fx Area) of airspace (a) and respiratory parenchyma (b) with age in SP-D (−/−) mice and age-matched SP-D (+/+) controls. Analysis of changes in these parameters with age for each individual genotype (c and d). Data are expressed as % fractional area and represent the mean± SE.

FIG. 16: RSV and IAV titers were determined by quantitative plaque assays of lung homogenates. Viral titers of RSV were significantly greater 3 and 5 days after administration of $10^7$ pfu RSV(Graph A) in SP-D −/− (open bar) compared to wild type (hatched bar) mice. Lung homogenate titers of IAV were significantly greater for SP-D −/− (open bar) compared to wild type (hatched bar) mice 3 and 5 days after infection (Graph B). Data are mean±SEM with n=15 mice per group (Graph A) and n=10 mice per group (Graph B). *p<0.05 compared to wild type mice.

DETAILED DESCRIPTION OF THE INVENTION

Figure 2:
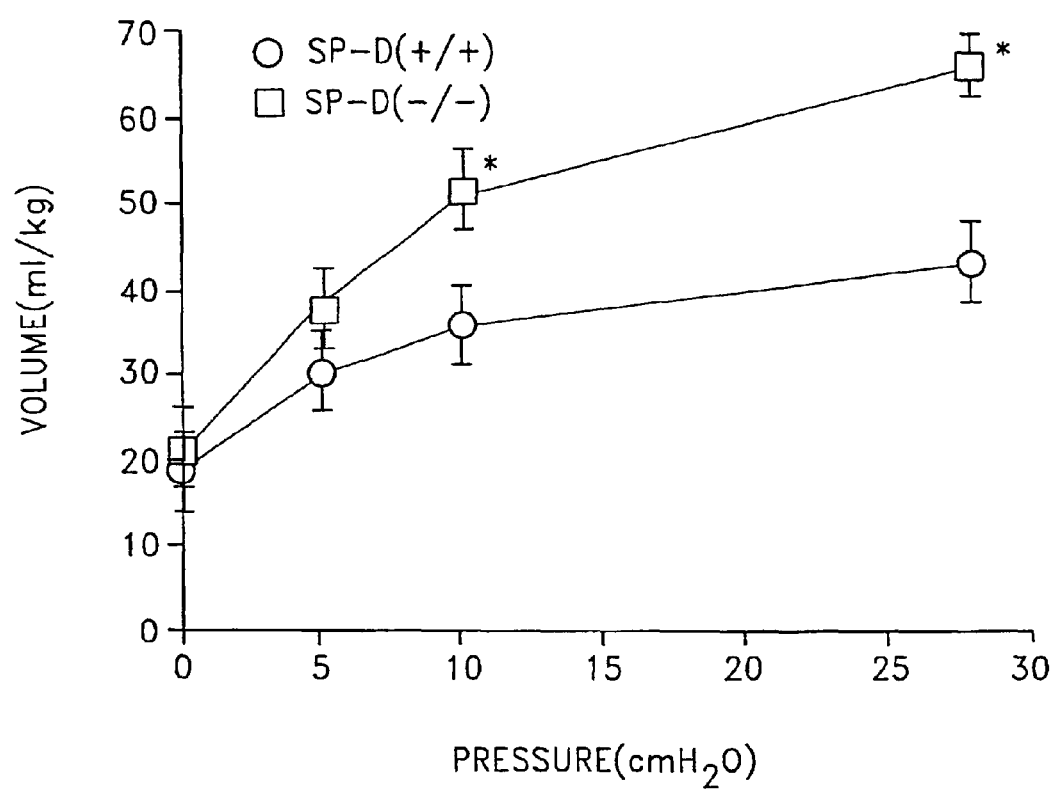
FIG. 2: Deflation limbs of pressure-volume curves from SP-D (+/+) and SP-D (−/−) mice. Data are expressed as ml/kg and represent the mean± SE.

We have produced an SP-D (−/−) knockout mouse to identify the role of SP-D in normal lung function and development and to demonstrate the temporal progression of postnatal airspace enlargement and spontaneous inflammatory changes in the lungs of these mice. SP-D (−/−) mice develop progressive pulmonary emphysema, associated with chronic inflammation and increased oxidant production by alveolar macrophages. The lung abnormalities make this mouse an excellent model for emphysema. Because there are very few existing therapies for treatment of emphysema, the most common being lung volume reduction surgery, the model is urgently needed. Based on the mouse model for emphysema, we have proposed a number of ways to test SP-D protein and expression vectors, and potential pharmaceuticals in the mouse model for efficacy in treating emphysema or other forms of chronic lung injury. We have also proposed the use of SP-D protein and expression vectors to treat various other diseases of aberrant surfactant production, pulmonary fibrosis, sarcoidosis, lung injury, toxicant/oxygen exposure, infection, increased oxidant exposure. Lastly, we have proposed using SP-D cDNA, SP-D antibodies, PCR, and differential hybridization techniques to identify patients at risk for emphysema, pulmonary distress syndromes, and other types of respiratory diseases. Although other materials and methods similar or equivalent to those described herein can be used in the practice or testing of the present invention, the preferred methods and materials are now described. Example 1 describes the steps required to produce the SP-D (−/−) mouse.

tailed with XhoI linkers and cloned into an XhoI site 5' from the neomycin-resistance cassette Eight of 104 ES clones surviving the double selection process were correctly targeted as determined by both 5' and 3' PCR analyses. Clone 93, a highly undifferentiated and proliferative clone, was expanded and injected into C57/B16 blastocysts generating chimeric males. Chimeric males were bred to NIH Swiss Black females. A female bearing the targeted gene was obtained and bred to NIH Swiss Black males to generate normal SP-D (−/−) and SP-D (±) mice. The distribution of genotypes from heterozygotic matings followed a Mendelian pattern, with 30 (+/+), 45 (+/−), and 25% (−/−) of 115 offspring, indicating that there were no obvious abnormalities in survival related to SP-D alleles.

SP-D(−/−) mice survive and breed normally in the vivarium under barrier containment facilities at Children's Hospital Medical Center, Cincinnati, Ohio. Mice have been viral free as assessed by serology. No serological evidence of viral infection in SP-D(−/−) mice was detected at necropsy.

To determine genotype, DNA from tail clips was digested with BamHI and probed with a PCR product derived from genomic mouse DNA, containing exon 2 and part of intron 2, and with the G418 resistance cDNA clone. This demonstrated a simultaneous loss of exon 2 with appearance of sequences encoding G418 resistance in SP-D (±) and SP-D (−/−) mice.

TABLE 1

Comparison of Body Weights, Lung Volumes, and Volume-to-Body Weight Rations (Mean ± SE)

| AGE | BODY WEIGHTS (g) | | LUNG VOLUMES (ml) | | LV:BW ($Ml/g \times 10^{-2}$) | |
|---|---|---|---|---|---|---|
| | SP-D (−/−) | SP-D (+/+) | SP-D (−/−) | SP-D (+/+) | SP-D (−/−) | SP-D (+/+) |
| 2 day | 1.8 ± 0.1* | 3.4 ± 0.1 | ND | ND | ND | ND |
| 5 day | 3.7 ± 0.3 | 4.6 ± 0.2 | ND | ND | ND | ND |
| 7 day | 3.9 ± 0.2* | 5.3 ± 0.2 | ND | ND | ND | ND |
| 14 day | 6.6 ± 0.2* | 7.7 ± 0.2 | ND | ND | ND | ND |
| 17 day | 10.9 ± 0.5 | 10.6 ± 0.7 | 0.36 ± 0.02 | 0.36 ± 0.03 | 3.25 ± 0.05 | 3.36 ± 0.03 |
| 3 wk | 10.9 ± 0.5* | 14.1 ± 1.2 | 0.36 ± 0.01 | 0.37 ± 0.03 | 3.43 ± 0.21** | 2.50 ± 0.18 |
| 6 wk | 23.2 ± 0.6 | 24.7 ± 0.5 | 0.63 ± 0.03 | 0.58 ± 0.02 | 2.71 ± 0.13** | 2.25 ± 0.18 |
| 9 wk | 25.2 ± 1.2 | 27.8 ± 1.3 | 0.55 ± 0.03 | 0.61 ± 0.02 | 2.10 ± 0.16 | 2.20 ± 0.09 |
| 28 wk | 36.9 ± 4.3 | 31.2 ± 1.6 | 0.67 ± 0.09 | 0.58 ± 0.06 | 2.03 ± 0.51 | 1.86 ± 0.10 |

*Significant statistical differences were observed in body weights at 2 day, p = 0.00001; 7 day, p = 0.0002; 2 wk, p = 0.007; and 3 wk, p = 0.04.
**Significant statistical differences in LV:BW rations were observed at 3 wk (p = 0.02), due to differences in body weight, and at 6 wk (p = 0.03), although body weights and lung volumes weere not statistically different at this latter time point. N = 3–7I animals per group. LV:BW, lung volume-to-body weight ratio; ND, not determined.

EXAMPLE 1

SP-D (−/−) Knockout Mouse Construction

SP-D (−/−) mice were generated by targeted gene inactivation. Integration of a pGKneo targeting vector containing sequences from exon 2 of the SP-D gene generated a deletion of the second exon of the SP-D gene, which included removal of the initiating methionine and translation initiation sequences. The mouse SP-D gene sequence of Exons 1 and 2 can be found under Genbank accession No. AF047741. The targeting vector was designed using pGKneo by first subcloning a 5.1-kb blunt ended KpnI-tailed HindIII genomic fragment encoding intron 2 through exon 6 into a KpnI site between the neomycin-resistance cassette and the thymidine kinase cassette. Subsequently, a 1.5-kb genomic PstI fragment containing a portion of intron I was To demonstrate that SP-D was not expressed in null animals, RNA blot analysis was conducted with total lung RNA from null, normal, and heterozygotic animals. The results showed approximately 50% reduction in the intensity of the SP-D hybridization band in heterozygous animals with a total absence of normally sized SP-D mRNA in null animals. After prolonged exposure, a diffuse mRNA band approximately 150 nucleotides smaller than the normal SP-D mRNA was detected. By scanning densitometry, this band represents less than 5% of the intensity of the normal SP-D transcript from heterozygous animals.

Western blot analysis of lung homogenates using rabbit anti-rat SP-D antiserum revealed SP-D was reduced approximately 50% in heterozygous SP-D (+/−) mice and was absent in SP-D (−/−) mice.

Both SP-D (−/−) and SP-D (+/−) mice survived normally in perinatal and postnatal periods. At selected ages, body, lung, and heart weights were obtained by direct measurement; and lung and heart volumes were obtained by fluid displacement. Lung protein and DNA content were assessed using bovine serum albumin and salmon sperm DNA, respectively, as standards. Body weights of SP-D (−/−) mice were slightly smaller prior to weaning, but were not significantly different from SP-D (+/+) mice after 3 weeks of age, Table 1. While lung volumes were not significantly different, lung-volume-to-body-weight ratios were increased in SP-D (−/−) mice at 3 and 6 weeks of age, Table 1. No significant differences were observed in heart volumes or heart-volume-to-body-weight ratios. At maturity (5 months), no changes in wet lung weight, total lung DNA or protein were noted.

However, while no abnormalities were observed in body weight, examples 2 through 5 describe the other abnormalities or changes found in SP-D (−/−) mice.

Example 2 demonstrates the effect on phospholipid levels. Alveolar and tissue phospholipid levels, specifically phosphatidylcholine pool levels, were markedly increased while total brochoalveolar lavage (BAL) protein levels remained unchanged.

EXAMPLE 2

Phospholipid Levels in the SP-D (−/−) Mouse

Alveolar, tissue and total saturated phosphatidylcholine (Sat-PC) ($p<0.001$) was increased about 3-fold in SP-D (−/−) mice. Levels of Sat-PC were not altered in SP-D (+/−) mice. For alveolar lavage phospholipid composition analysis, two to four samples consisting of the pooled lavage from two to three mice were evaluated for the relative abundance of phosphatidylcholine, phosphatidylethanolamine, phosphatidylglycerol, phosphatidylinositol, sphingomyelin, and lyso-bis-phosphatidic acid. Phospholipid composition did not differ among genotypes. Incorporation of ($^3$H)choline into total lung Sat-PC was slightly increased 8 hr following injection, incorporation being approximately 20% greater in SP-D (−/−) mice ($p<0.05$).

This result was completely unexpected in that previous work suggested a definite role for SP-A and a limited role for SP-D in lung phospholipid homeostasis. Previous diseases associated with surfactant homeostasis involved accumulations of both surfactant proteins and lipids, thus the SP-D (−/−) null mouse demonstrates for the first time that SP-D is an important player in surfactant lipid homeostasis and that surfactant lipid and protein homeostasis can be dissociated in vivo, since the total protein concentration in the surfactant did not change. However, there was a modest decrease in the total concentration of SP-A as explained in example 3.

EXAMPLE 3

Reduction in SP-A Levels in the SP-D (−/−) Mouse

No differences in SP-B and SP-C mRNAs or proteins were observed in SP-D (−/−) mice. In contrast, Northern blot hybridization of total lung RNA from SP-D (+/+), SP-D (+/−), and SP-D (−/−) mice and hybridization with and SP-A probe showed that SP-A mRNA was reduced in SP-D (−/−) mice. Consistent with the reduction in SP-A mRNA, BAL SP-A protein was apparently reduced by about 25% in SP-D (−/−) mice as assessed by Western blot analysis of alveolar lavage from three mice.

Therefore, SP-D has a role in the regulation of SP-A production. Since SP-A is involved in host defense in the lungs, SP-D can affect host defense in two ways. By up-regulation of SP-A production and by direct interaction with immune and microbial cells.

The ultrastructure of the phospholipid rich material isolated form the BAL of the SP-D (−/−) mice was evaluated as explained in example 4.

EXAMPLE 4

Changes in Surfactant Stucture in SP-D (−/−) Mouse

Large aggregate surfactant was isolated from pooled alveolar lavage of SP-D (−/−) and SP-D (+/+) mice and examined by EM using the technique outlined below. Lipid aggregates in SP-D (−/−) mice were enlarged and organized into electron dense phospholipid arrays and contained less tubular myelin compared with SP-D (+/+) mice. The ultrastructure proved to be markedly abnormal, containing reduced quantities of tubular myelin and forming unique densely packed lipid structures. Therefore, SP-D has a role in the structural organization of alveolar lipids.
Aggregate Forms from Alveolar Lavage Surfactant in alveolar was can be separated into large aggregate (heavy, dense) and small aggregate (light, visicular) fractions by centrifugation. Alveolar washes were centrifuged at 40,000×g over 0.8 M sucrose cushion for 15 min. The large aggregate surfactant then was collected from the interface, diluted with normal saline and centrifuged again at 40,000×g for 15 min. The supernatant from the first 40,000×g centrifugation that contains small aggregate surfactant is concentrated at 4° C. by ultrafiltration using a 300,000 molecular weight retention filter (Minitan, Miliore Corp., Bedford, Mass.) or centrifugal concentrators (Amicon Corp., Danvers, Mass.). The small aggregate surfactant is diluted with 50 ml normal saline and ultrafiltered 3 times to remove soluble proteins.

Lastly, the structure of the lung was analyzed. Although, normal in SP-D (+/−) mice, increased numbers of large foamy alveolar macrophages and enlarged alveoli were observed in SP-D (−/−) mice. In example 5 the method and results for identifying lung abnormalities is outlined.

EXAMPLE 5

Lung Abnormalities in the SP-D (−/−) Mouse

To determine whether absence of SP-D expression led to structural abnormalities, lungs from null, normal, and heterozygous mice were inflation fixed, and morphology and histochemical analysis was done on sections by light microscopy. There was no evidence of infection and no obvious alterations in airway epithelial cells at the level of light microscopy. However, heterogeneous abnormalities in lung parenchyma, with enlarged alveoli, were consistently observed in the SP-D (−/−) but not SP-D (+/−) or SP-D (+/+) controls.
Morphological and Histochemical Method Lung tissue from SP-D (+/+) and SP-D (−/−) mice were sacrificed at 2 weeks, 3 weeks and 6 weeks. Animals were weighed, anesthetized with a 4:1:1 mixture of ketamine, acepromazine and xylazine, and exsanguinated by severing the inferior vena cava and descending aorta. The trachea was cannulated, and the lungs were collapsed by piercing the diaphragm. The lungs were inflation-fixed at 25 cm of water pressure with 4% paraformaldehyde in phosphate buffered saline (PBS) for 1 minute. The trachea was tied off as the cannula was removed in order to maintain the fixative in the inflated lung. Excised lungs and heart were allowed to equilibrate in cold fixative until they had sunk to the bottom of the container. Lung and heart volumes were then determined by fluid displacement. Each lobe was measured along its longest axis, bisected perpendicularly to the long axis, and processed into paraffin blocks. Five micron sections were cut in series throughout the length of each lobe, loaded onto polysine-coated slides, and stained with hematoxylin and eosin, Masson's trichrome stain for collagen, or ocein for elastin.

Lung Morphology

In more detail, examination within the first 2 weeks of life demonstrated no detectable abnormalities in lung morphology, although increased numbers of normal appearing alveolar macrophages were noted in the alveoli of SP-D (−/−) mice at 14 days of age. In contrast abnormalities in lung histology were observed in SP-D (−/−) mice at 3 and 6 weeks of age consisting of enlarged airspaces and infiltration with atypical, foamy, alveolar macrophages. Enlarged airspaces associated with the accumulation of hypertrophic, foamy, alveolar macrophages and perivascular/peribronchiolar monocytic infiltrates were observed by 6 to 7 months of age, although the extent of airspace enlargement in individual SP-D (−/−) mice varied from moderate to severe in this age group.

In 7 month old SP-D (−/−) mice, subpleural fibrotic lesions were observed that stained intensely for collagen. Abnormalities in elastin deposition were also observed in the parenchyma of lungs from SP-D (−/−) mice at this time point. These consisted of regions of lung parenchyma with short thick, and more highly coiled elastic fibers, as well as regions of inflammation where elastin staining was decreased in adjacent alveolar septa (adjacent to macrophage accumulation and fibrosis).

Increased bronchial-associated lymphocytic tissue (BALT) was noted in the SP-D (−/−) mice. Intensity of SP-B immunostaining in type II cells was similar among the three genotypes. Type II cells were purified as outlined below. However, there were focal areas of increased numbers of large, foamy intra-alveolar cells, which appeared to be alveolar macrophages containing abundant cytoplasmic vesicles. These cells increased in size as a result of increasing number and volume of cytoplasmic vesicles. The vesicles stained with Nile Red and fluoresced when excited with 520–550 nm green light after staining with Nile Blue and thus contained lipid or phospholipid. These macrophages were also stained by SP-B antiserum. In alveolar lavage, approximately 4-fold more macrophages ($1.2 \times 10^6$ per mouse) were observed in SP-D (−/−) compared with normal mice ($0.36 \times 10^6$/mouse), but there were no changes in relative neutrophil or lymphocyte cell counts. Macrophage size was estimated from the diameter of fixed and stained macrophages from cytospin preparations sedimented onto glass slides at 1500×g for 2 min. Mean diameter of macrophages from (+/+) was 11.75±1.75 $\mu$m compared with (−/−) mice 18.75±7.25 $\mu$m. Abnormally large macrophages, defined as those with a diameter of twice normal, comprised 22.4±10.6% of the macrophages from (−/−) mice compared with 18±1.0% from (+/+) mice. Numbers and morphology of alveolar macrophages were not different in SP-D (+/−) mice. Ultrastructural characteristics of type II cells were similar in SP-D (−/−) compared with SP-D (+/+) mice. The morphology of the alveolar macrophages is consistent with that of activated "foam" cells, known to be associated with inflammation.

Isolation of Murine Type II Cells

Type II cells are routinely isolated in this laboratory using the following method. Mice are anesthetized by intraperitoneal injection and pentobarbital (50 mg/ml 3.25 ml/kg body weight). After opening the abdominal cavity, mice are exsanguinated by severing the inferior vena cava. The trachea is exposed, cannulated with a 20 gauge luer stub adaptor, and secured by a suture. The chest plate is removed and lungs perfused with 10–20 ml sterile saline via the pulmonary artery until visually free of blood. Dispase (Collaborative Research, Inc., Bedford, Mass.) is instilled into the lungs via the tracheal catheter, followed by 1% low melt agarose, warmed to 45° C. Lungs are immediately covered with ice and incubated for 2 minutes to set the agarose. Lungs are dissected out, put in a culture tube containing an additional 1 ml Dispase, and incubated for 45 minutes at room temperature. Lungs are next transferred to a 60 mm culture dish containing 100 U/ml DNAase 1 (Sigma, St. Louis, Mo.) in 7 ml DMEM (Gibco BRL, Gaithersburgh, Md.). The tissue is gently teased away from the airways and swirled for 5 minutes. Cells are then placed on ice until being filtered. The cell suspension is successively filtered through 10 $\mu$m and 40 $\mu$m cell strainers, and then through 25 $\mu$m nylon gauze (Tetko, Briarcliff Manor, N.Y.). Cells are pelleted for 7 min at 130×g at 4° C. and resuspended in 10 ml DMEM with 10% FBS (Intergen Co., Purchase, N.Y.). Crude cell suspensions are added to 100 mm culture dishes that were previously coated with CD-45 and CD-32 antibodies (Pharmigen. San Diego, Calif.) and incubated for 102 hours at 37° in the presence of 5% $CO_2$. Plates are removed from the incubator and gently "panned" to free settled type II cells. The cell suspension is centrifuged at 130×g at 4° C. and resuspended in 10 ml DMEM with 10% FBS (Intergen Co., Purchase, N.Y.). Crude cell suspensions are added to 100 mm culture dishes that were previously coated with CD-45 and CD-32 antibodies (Phannigen. San Diego, Calif.) and incubated for 102 hours at 37° C. in the presence of 5% $CO_2$. Plates are removed from the incubator and gently "panned" to free settled type II cells. The cell suspension is centrifuged at 130×g for 7 minutes and cells are resuspended in DMEM containing 10% FBS.

Airspace and Respiratory Parenchyma

Morphometric measurements were performed on mice at 5 days (0.5 weeks), 14 days (2 weeks) and 17 days (2.5 weeks), 3 and 6 weeks, and 6 to 7 months of age. the overall proportion (% fractional area) of respiratory parenchyma and airspace was determined using a point counting method. Measurements were performed on sections taken at intervals throughout the left, right upper, or right lower lobes. Slides were viewed using a 20× objective, and the images (fields) were transferred by video camera to a computer screen using MetaMorph imaging software (Universal Imaging Corp., West Chester, Pa.). A computer-generated, 121-point lattice grid was superimposed on each field, and the number of intersections (points) falling over respiratory parenchyma (alveoli and alveolar ducts) or airspace was counted. Points falling over bronchioles, large vessels, and smaller arterioles and venules were excluded from the study. Fractional areas (% Fx Area) were calculated by dividing the number of points for each compartment (n) by the total number of points contained within the field (N), and then multiplying by 100:

$$\% \ F \times \text{Area} = n/N \times 100$$

Ten fields per section were analyzed to gather the data. The x and y coordinates for each field measured were selected using a random number generator.

While, as shown in FIG. 1, no differences in the relative proportion (% fractional area) of airspace (a) and respiratory parenchyma (b) were observed at 5 days (0.5 weeks), 14 days (2 weeks), or 17 days (2.5 weeks) of age, the % fractional area of airspace was increased significantly (p=0.013) in SP-D (−/−) mice by 3 weeks of age. More specifically, the fractional area devoted to both airspace (a) and parenchyma (b) diverged significantly between the two different genotypes at 3 weeks (*p=0.013), 6 weeks (*p=0.0007), and 28 weeks (*p=0.004) of age. Likewise, the % fractional area of respiratory parenchyma was decreased in SP-D (−/−) mice compared to age-matched SP-D (+/+) controls (34% parenchyma/66% airspace compared to 42.5% parenchuma/57.5% airspace, respectively), FIG. 1. Relative proportions of airspace and respiratory parenchyma continued to diverge significantly from controls at later time points, the % fractional areas ranging from 27% parenchyma/73% airspace to 37% parenchyma/63% airspace in 7 month old SP-D (−/−) mice (n=5). Age-matched SP-D (+/+) controls showed less variability, ranging from 45% parenchuma/55% airspace to 47% parenchyma/53% airspace, at this time point (n=4). The overall percent reduction in parenchyma at 7 months of age in the SP-D (−/−) mice was 32% of control values, while the percent increase in airspace in the SP-D (−/−) mice was 27% of control values.

Cellular Proliferation

Animals were pre-injected with BrdU 4 hours prior to sacrifice in order to assess alterations in cellular proliferation. Immunohistochemical detection of incorporated BrdU was performed using a commercially available kit (Zymed Laboratories, Inc., San Francisco, Calif.). Sections of small intestine from each animal were immunostained in parallel with the lung sections as a positive control for BrdU incorporation.

BrdU labeling indices were relatively low, and no changes in BrdU labeling of respiratory parenchymal cells or alveolar macrophages were observed in the lungs from SP-D (−/−) mice compared to controls.

Lung Volumes

Determination of lung volumes using pressure-volume curves was as follows: Twelve week-old mice were injected with sodium pentobarbital and placed in a chamber containing 100% oxygen to ensure complete collapse of alveoli by oxygen absorption. Mice were killed by exsanguination, the trachea cannulated and connected to a syringe linked to a pressure sensor via a three-way connector (Mouse Pulmonary Testing System, TSS Incorporated, Cincinnati, Ohio). After opening the diaphragm, lungs were inflated in 75 $\mu$l increments every 10 seconds to a maximum pressure of 28 cm of water and then deflated. Pressure-volume curves were generated for each animal, determining lung volumes (divided by body weight) at 10, 5, and 0 cm of water during the deflation curve. In FIG. 2, pressure-volume curves were generated in 5–6 mice at 12 weeks of age. Lung volumes associated with the deflation limbs of pressure-volume curves were significantly greater for 12 week old SP-D (−/−) mice compared age-matched to SP-D (+/+) mice at 10 cm $H_2O$ and at the maximum pressure of 28 cm $H_2O$ (*p<0.05).

Statistically significant differences were determined by using either analysis of variance for fractional areas and pressure-volume curves, followed by the Student-Newman-Keuls procedure, or the student's T test for comparison of body weights, lung and heart volumes, volume:body weight ratios, total protein and DNA content. Differences of p<05 were considered significant. Values are given as mean±SE.

Increased lung volumes were readily apparent in SP-D (−/−) mice at 12 weeks of age, consistent with histologic and morphometric studies demonstrating emphysema, see FIG. 2.

Alveoli

The enlarged alveoli were consistently observed in the SP-D (−/−) mice. Therefore, SP-D is very likely to be involved in the regulation of alveolar remodeling in the lungs. Because abnormalities and airspace remodeling is a defining characteristic of emphysema, the SP-D (−/−) mouse is an ideal model for emphysema.

EXAMPLE 6

Cytokines, Hydrogen Peroxide Production, and Metalloproteinase Activities

Methods

Cytokine Measurements

Lung homogenates from 6 to 9 week-old mice were centrifuged at 2000 RPM and stored at −20° C. Tumor necrosis factor alpha (TNF-α), interleukin (IL)-1β, IL-6, and macrophage inflammatory protein (MIP)-2 were quantitated using murine sandwich ELISA kits (R&D Systems, Minneapolis, Minn.) according to the manufacturer's directions. All plates were read on a microplate reader (Molecular Devices, Menlo Park, Calif.) and analyzed with the use of a computer-assisted analysis program (Softmax; Molecular Devices). Only assays having standard curves with a calculated regression line value of >0.95 were accepted for analysis.

Hydrogen Peroxide Production

Alveolar macrophages were collected by bronchoalveolar lavage with 1 ml of dye-free RPMI media (Gibco, Grand Island, N.Y.) times three. Bronchoalveolar lavage fluid (BALF) from 8–10 mice was pooled to provide sufficient numbers of macrophages for analysis. The lavage was centrifuged at 1200 RPM for 10 minutes and one million macrophages were resuspended in PBS. Hydrogen peroxide production by macrophages was measured using a commercially available assay (Bioxytech $H_2O_2$-560 assay, OXIS International, Portland, Oreg.), based on the oxidation of ferrous ions ($Fe^{2+}$) to ferric ions ($Fe^{3+}$) by hydrogen peroxide under acidic conditions. Methods followed the manufacturer's recommendations. Hydrogen peroxide production was determined after activation with 100 ng/ml phorbol myristate acetate (PMA) or without stimulation.

Metalloproteinase Activity

Mouse lavage samples were centrifuged (100,000×g, 1 hour) in a SW-28 rotor (Beckman, Palo Alto, Calif.). The supernatants were concentrated using Centricon-30 filtration units (Amicon, Inc., Beverly, Mass.). Samples (200 $\mu$g protein) were electrophoresed under nonreducing conditions (laemmli) into 10% Zymogram, gelatin and casein gels (Novex, San Diego, Calif.). Following electrophoresis, gels were washed twice with 2.5% Triton X-100 (37° C., 15 min.) and incubated for 16 hours with 40 mM Tris-HCl, pH 7.5, 10 mM $CaCl_2$, 1 uM $ZnCl_2$. Gels were stained with 0.5% (w/v) Coomassie Blue in 50% methanol, 10% acetic acid for 1 hour, then destained. Metalloproteinases were detected as clear bands against the blue background. Metalloproteinase 2 and 9 mRNA's were quantitated by Northern blot analyses of total lung mRNA from wild type and SP-D (−/−) mice using [$^{32}$P]-labeled cDNA probes (Chemicon International, Inc., Temecula, Calif.).

Results

Figure 3:
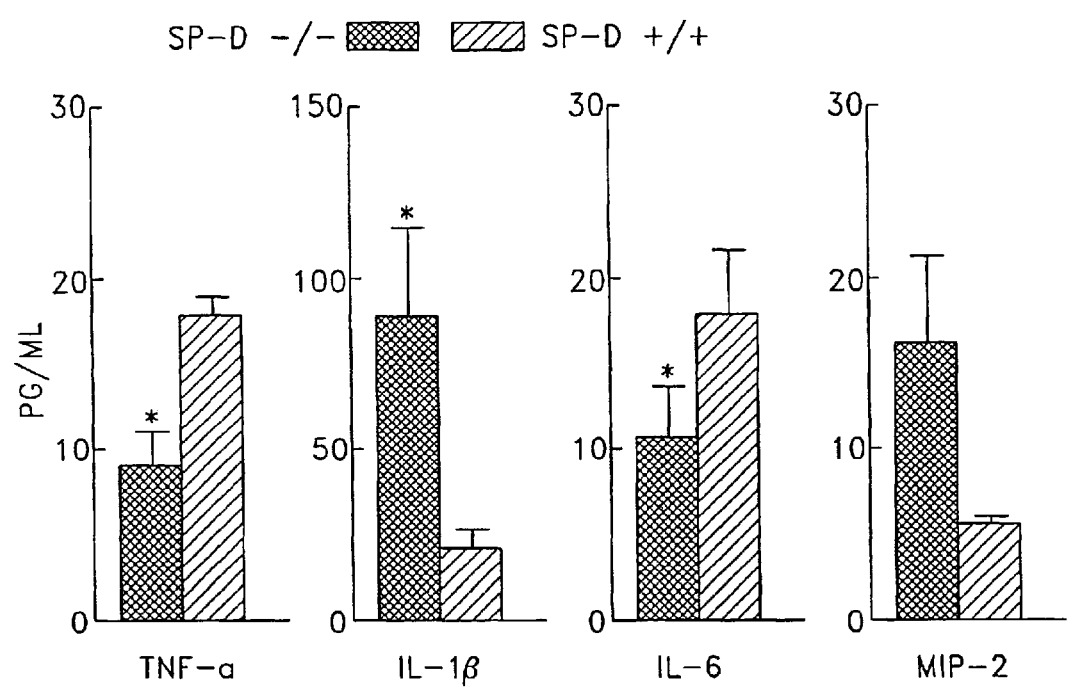
FIG. 3: Pro-inflammatory cytokines in lung homogenates from SP-D (−/−) mice. Concentrations of TNF-α, IL-1β, IL-6 and MIP-2 were assessed in lung homogenates from SP-D (−/−) (solid bar) and SP-D (+/+) (hatched bar) mice. Data are expressed as pg/ml and represent the mean±SE with n=5 mice per group; *p<0.05 compared to SP-D (+/+) mice.
Figure 4:
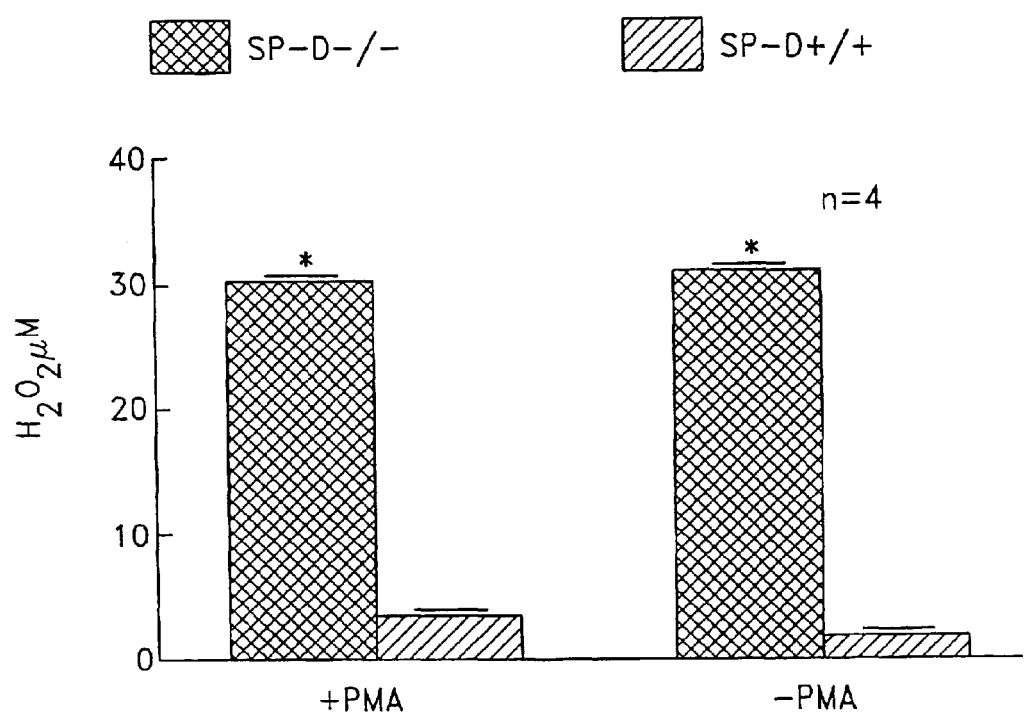
FIG. 4: Hydrogen peroxide production in alveolar macrophages from SP-D (−/−) (solid bar) was assessed from $1 \times 10^6$ macrophages isolated from broncho alveolar lavage fluid (BALF) as compared to SP-D (+/+) mice (hatched bar) with and without PMA stimulation. Data are expressed as $\mu M$ of $H_2O_2$ and represent the mean±SE with n=4 mice per group; *p<0.05 compared to SP-D (+/+) mice.

At 6 to 9 weeks of age, lung homogenates from SP-D (−/−) mice did not contain inflammatory levels of the pro-inflammatory cytokines TNF-α, IL-1β, IL-6 or MIP-2, although basal levels of IL-1β were increased significantly, FIG. 3. In contrast, oxidant production, as assessed by measuring hydrogen peroxide production by alveolar macrophages isolated from SP-D (−/−) mice, was increased 10 fold, FIG. 4. Hydrogen peroxide and superoxide production is a measure of macrophage activation, particularly the microbicidal activation. Since oxidant production has been associated with activation of a number of metalloproteinases and with emphysema in both human and animal studies, metalloproteinase activities were estimated by degradation of gelatin substrates after SDS-PAGE of BALF supernatants isolated from SP-D (−/−) and SP-D (+/+) mice. Bands of activity consistent with metalloproteinases-2 and -9 were readily detected in both genotypes, but were not altered in lung tissue from SP-D (−/−) mice. Likewise, the abundance of metalloproteinasese-2 and -9 mRNA's were similar in whole lung RNA samples from SP-D (−/−) and SP-D (+/+) mice as assessed by Northern blot analysis. However, production of MMP-2 and 9 by alveolar macrophages isolated from SP-D (−/−) mice were markedly increased. Likewise, immuno-staining for MME (macrophage metalo-elastase) and MMP-9 were increased in the lungs of the SP-D (−/−) mice.

The results in Examples 1–6 were completely unexpected. There is nothing in the literature to suggest an SP-D null mouse is a model for emphysema.

In summary, the SP-D (−/−) mouse conclusively demonstrates a remarkable and surprising role for SP-D in regulation of surfactant homeostasis, the structure of alveolar surfactant in the lung, regulation of SP-A expression, or plays a critical inhibitory role in oxidant, hydrogen peroxide production in the lung. Therefore, its levels are important for suppression of ongoing oxidant production and injury and the regulation of alveolar remodeling and suppression of proteases that cause emphysema. This makes the SP-D (−/−) mouse an excellent model for emphysema. Example 7 will summarize the results for the mouse model of emphysema.

EXAMPLE 7

SP-D (−/−) Mouse as a Model for Emphysema

SP-D deficiency caused inflammation, increased oxidant production by isolated alveolar macrophages, emphysema, and localized fibrosis in gene-inactivated SP-D (−/−) mice. The timing and progressive nature of these pulmonary abnormalities support the conclusion that alveolar enlargement in SP-D (−/−) mice is caused by alveolar remodeling associated with chronic inflammation, rather than with development abnormalties occurring during alveologenesis. The present findings are consistent with an important and unanticipated role of SP-D in the modulation of pulmonary inflammation and oxidant production and suggest that changes in the regulation or function SP-D may play a role in the pathologic processes leading emphysema following chronic lung injury.

Histologic and morphometric analyses of lungs from SP-D (−/−) mice revealed no abnormalities in lung structure until 3 weeks of postnatal age, one week after alveologenesis is completed in the mouse. This was consistent with the observation that the relative proportions of respiratory parenchyma and airspace were similar in both SP-D (−/−) and SP-D (+/+) mice between postnatal days 5 and 17. After 2 weeks of age, increased parenchymal-airspace ratios were observed in SP-D (−/−) mice, consistent with ongoing remodeling of the parenchyma and alveolar spaces. Enlarged airspaces were generally associated with focal accumulation of large, foamy, alveolar macrophages, although there was some heterogeneity in both localization and extent of inflammatory infiltrates and remodeling in older mice While focal accumulation of alveolar macrophages in lungs of SP-D (−/−) mice were observed as early as 2 weeks of age, macrophage morphology remained normal at this time. Abnormal alveolar macrophage morphology, consisting of enlarged foamy cells, was noted by 3 weeks of age and was coincident with enlargement of alveolar structures thereafter. Previous studies demonstrated increased numbers of enlarged alveolar macrophages in SP-D (−/−) mice by 8 weeks of age. Thus, the development of emphysema in SP-D (−/−) mice is consistent with the temporal and spatial accumulation of activated macrophages, and increased production of proteases MMP-2, 9 and MME, suggesting their role in the remodeling process. The present findings do not support a role for SP-D in normal long morphogenesis and alveologenesis, a process generally completed by approximately 2 weeks of postnatal age in mice.

The present findings do support an important role for SP-D in the modulation of alveolar macrophage activation and oxidant production, leading to protease activation, emphysema and fibrosis. Macrophage infiltration and lung remodeling in SP-D (−/−) mice were associated with modest but significant differences in inflammatory levels of various pro-inflammatory mediators, including IL-1b, MIP-2, but not TNF-α and IL-6, but rather with markedly increased hydrogen peroxide production by isolated alveolar macrophages. Although basal levels of IL-β1 were significantly increased in SP-D (−/−) mice, IL-β1 was not increased to levels typically detected in severe inflammation. While increased IL-1β and hydrogen peroxide production were observed in SP-D (−/−) mice, it remains unclear whether the pulmonary abnormalities seen in these mice were directly mediated by cytokine or oxidant-induced injury. Although SP-D has been proposed to play an important role in host defense, there was no histologic or serologic evidence of infection in the SP-D (−/−) colony.

Enhanced hydrogen peroxide production and increased numbers of alveolar macrophages found in the lungs of SP-D (−/−) mice support the concept that SP-D plays a critical anti-inflammatory role in the lung and regulates hydrogen peroxide production by alveolar macrophages in vivo. Relationships between oxidant injury and the development of emphysema and pulmonary fibrosis are well established in numerous animal and genetic models. For example, neonatal exposure to hyperoxia caused alveolar remodeling and fibrosis in newborn mice. Since activation of metalloproteinases has been associated with oxidant injury and emphysema, metalloproteinase activities were assessed in BALF from the SP-D (−/−) mice. While protease activity consistent with metalloproteinase -2 and -9 were readily detected by zymography in lung homogenates, but, no consistent changes in the activities of these proteinases or their mRNAs were detected in SP-D (−/−) mice. However, markedly increased production of MMP-2 and MMP-9 were demonstrated in isolated alveolar macrophages from SP-D (−/−) mice in vitro and immuno-staining for MME and MMP-2 were increased in the lungs of SP-D (−/−) mice in vivo. Thus, localized increased concentrations of metalloproteinases and/or alterations in other proteases or antiproteases is associated with SP-D deficiency. Deficiencies in antiproteases, as well as smoking and oxidant injury from oxidizing toxicants (e.g., bleomycin or paraquat), have all been associated with emphysema or pulmonary fibrosis in human lung.

While surfactant phospholipid content was increased in SP-D (−/−) mice and was associated with increased numbers of large, foamy, alveolar macrophages, increased phospholipid content alone is not likely to be sufficient to cause the alveolar remodeling observed in SP-D (−/−) mice. In fact, the overall effect of surfactant phospholipids appears to be anti-inflammatory, altering phagocytosis, oxidant production, and cytokine release, and inhibiting lymphocyte proliferation, immunoglobulin production, and expression of adhesion molecules. On the other hand, transgenic mice in which GM-CSF was over-expressed in the respiratory epithelium had markedly increased numbers of normal appearing alveolar macrophages, but did not develop pulmonary alveolar proteinosis/lipoidosis, emphysema, or fibrosis. In contrast, surfactant phospholipids and proteins were markedly increased in lungs from both GM-CSF (−/−) and GM-receptor common beta subunit (βc) deficient mice in association with alveolar macrophage accumulation and perivascular/peribronchiolar monocyte infiltrates; however, neither model of pulmonary alveolar proteinosis/lipoidosis was associated with emphysema or fibrosis. Likewise, transgenic mice over-expressing IL-4 in the lung also exhibited increased amounts of surfactant protein and lipids, as well as increased numbers of inflammatory cells, but did not develop emphysema.

Although concentrations of SP-D in the lung change during development, increasing with advancing age, SP-D levels are also influenced by various clinical conditions. Recent studies demonstrated marked reduction of SP-D concentrations in BALF obtained from patients with cystic fibrosis (CF), supporting a potential role for SP-D in the pathogenesis of the chronic inflammation associated with CF lung disease. SP-D levels were also reduced in BALF of smokers, suggesting that decreased levels of SP-D may contribute to later development of chronic obstructive pulmonary disease (COPD) and emphysema in these patients. Although concentrations of SP-D in BALF were increased in patients with pulmonary alveolar proteinosis (PAP), patients with idiopathic pulmonary fibrosis (IPF) and interstitial pneumonia associated with collagen vascular disease (IPCD) had decreased BALF levels of SP-D. On the other hand, serum concentrations of SP-D were increased in patients with PAP, IPF, and IPCD; although serum levels of both SP-A and SP-D varied with the severity of IPF and during the course of anti-inflammatory therapies. These clinical findings, as well as the present study, demonstrating that SP-D is required for maintenance of normal lung architecture and suppression of oxidant production, support the concept that changes in SP-D concentrations may be involved in the pathogenesis of lung injury associated with various clinical conditions, including oxidant injury, lung abcesses, secondary diseases, cystic fibrosis, interstitial pumonary fibrosis (IPF), and chronic obstructive pulmonary disease (COPD), various lung infections, respiratory distress syndrome (RDS), bronchopulmonary dysplasia (BPD), chemotherapy-induced lung injury, lung fibrosis secondary to primary abcess (ie: sarcoid), and asthma.

In our previous studies, no abnormalities in alveolar macrophages or lung morphology were observed in the heterozygous SP-D (+/−) mice, demonstrating that a 50% reduction in SP-D concentration in BALF is not sufficient to cause pulmonary abnormalities. The precise concentrations of SP-D that are required for inhibition of oxidant-induced injury and lung remodeling are unclear at present. Whether further injury or oxidant stress to the lungs of SP-D (+/−) or SP-D (−/−) mice will exacerbate emphysema and fibrosis in this animal model remains to be determined.

The modest reduction of lung SP-A concentrations found in SP-D (−/−) mice is not likely to contribute to the changes in lung morphology observed in these mice, since neither SP-A (+/−) nor SP-A (−/−) mice developed emphysema. Furthermore, lung morphology of SP-A deficient mice was normal, and, in contrast to SP-D (−/−) mice, SP-A deficiency was associated with decreased hydrogen peroxide production by isolated alveolar macrophages.

SP-D (−/−) mice developed severe and progressive emphysema. Alveolar remodeling and macrophage abnormalities were apparent as early as 3 weeks of age, while mild, focal, pulmonary fibrosis was observed at 6 to 7 months of age, demonstrating a role for SP-D in the regulation of inflammation and alveolar remodeling. The present study also demonstrated an unexpected role for SP-D in the regulation of hydrogen peroxide production and metalloprotease production by alveolar macrophages in vivo, which may contribute to the development of emphysema in the lungs of SP-D (−/−) mice. Whether SP-D deficiency contributes to ongoing inflammation or to the development of emphysema and fibrosis found in various human chronic lung diseases, including those caused by smoking and other oxidants, remains to be determined.

Testing Therapies in the Mouse Model

Because of the lack of pharmaceutical therapies for the treatment of emphysema, a model for testing possible therapies is imperative. The SP-D (−/−) mouse provides that model. Therefore, Example 6 provides a sample framework for testing pharmaceuticals, protein preparations, or genetic manipulations for the treatment of emphysema.

EXAMPLE 8

A number of doses or concentrations of protein or pharmaceutical diluted in an appropriate buffer is administered to SP-D (−/−) mice intratracheally. Protein and pharmaceutical is purified as appropriate for in vivo use. Recombinant adenovirus or other genetic vectors containing the gene of interest is administered as follows. SP-D (−/−) mice are immunosuppressed to block specifically T cell-mediated immune responses, and treated with an adenoviral construct designed to express the gene of interest in transduced cells. Mice are injected intraperitoneally with H57 antibody 3 days prior to receiving the adenoviral construct. H57 alters immune recognition at the T cell receptor and decreases splenic and lung T and B lymphocytes. One dose is instilled intratracheally and another group is treated intraperitoneally with H57 followed by intratracheal administration of vehicle alone. Levels of the protein of interest is measured 1 week after administration to detect uptake and expression of the vector. Four mice are tested and untreated SP-D (−/−) mice are used as a control. Intratracheal inoculation involves anesthetizing with isofluorane, and an anterior midline incision is made to expose the trachea. A 30-gauge needle attached to a tuberculin syringe is inserted into the trachea, and a 100-$\mu$l inoculum of protein or pharmaceutical is dispersed into the lungs. The incision is closed with one drop of Nexaband. Nonpyogenic PBS is injected intratracheally as a control.

To test for efficacy of the protein, pharmaceutical, or genetic manipulation at diminishing the effects of emphysema, a number of tests are performed.

To determine the effects of the protein or pharmaceutical on the lung structure lungs are inflation fixed and sections evaluated by electron microscopy. Lungs from treated and untreated mice are inflated via a tracheal cannula at 20 cm of pressure with 4% paraformaldehyde and removed en bloc from the thorax. Lungs are dehydrated and embedded in paraffin. Tissue sections (5 $\mu$m) are stained with hematoxylin and eosin.

To test the number and morphology of macrophages: Staining with Nile Red detects vesicles and staining with Nile Blue and exciting with 520–550 mm green light is an additional method to detect lipid or phospholipid. Macrophage number is determined by staining with anti MAC-1 or other macrophage specific antiserum. Macrophage size is estimated from the diameter of fixed and stained macrophages from cytospin preparations sedimented onto glass slides at 1500×g for 2 min.

Surfactant composition and ultrastructure is analyzed as follows: The structure of surfactant is analyzed by isolating large aggregates from pooled alveolar lavage of SP-D (−/−) treated and untreated mice and examined by EM (see protocol below). For alveolar lavage phospholipid composition analysis, two to four samples consisting of the pooled lavage from two to three mice are evaluated for the relative abundance of phosphatidylcholine, phosphatidylethanolamine, phosphatidylglycerol, phosphatidylinositol, sphingomyelin, and lyso-bis-phosphatidic acid. Incorporation of ($^3$H)choline into total lung Sat-PC is evaluated to determine total phospholipid concentration Aggregate Forms from Alveolar Lavage Surfactant in alveolar was can be separated into large aggregate (heavy, dense) and small aggregate (light, visicular) fractions by centrifugation. Alveolar washes were centrifuged at 40,000×g over 0.8 M sucrose cushion for 15 min. The large aggregate surfactant then was collected from the interface, diluted with normal saline and centrifuged again at 40,000×g for 15 min. The supernatant from the first 40,000×g centrifugation that contains small aggregate surfactant is concentrated at 4° C. by ultrafiltration using a 300,000 molecular weight retention filter (Minitan, Miliore Corp., Bedford, Mass.) or centrifugal concentrators (Amicon Corp., Danvers, Mass.). The small aggregate surfactant is diluted with 50 ml normal saline and ultrafiltered 3 times to remove soluble proteins.

SP-D as a Treatment for Pulmonary Diseases

Because deletion of SP-D produced the mouse model for emphysema, SP-D is an obvious choice as a treatment for or prevention of emphysema. It is also an obvious treatment for other types of pulmonary disease since many of these diseases are characterized by aberrant surfactant production. In addition, its affect on SP-A and its possible role in host defense makes it a useful tool to augment immune function in the lungs. The feasibility of gene transfer to the respiratory epithelium is very promising as a treatment for various pulmonary diseases. A variety of viral and non-viral-based vectors have been developed to transfer genes to cells of the airways, including recombinant adenoviral vectors. These vectors are particularly promising for use in respiratory treatment because they have the potential of being aerosolized. Therefore, Example 9 is an experiment using purified mouse SP-D protein for treatment of emphysema in SP-D(−/−) mice. Example 10 is an experiment using adenovirus to express rat SP-D for treatment of emphysema in SP-D(−/−) mice. Example 11 provides a sample framework for the use of SP-D peptide, or vectors expressing SP-D for the prevention and treatment of these diseases. Emphysema is used as an exemplary pulmonary disease. Adenovirus is used as an exemplary vector.

Treatment with Purified SP-D

EXAMPLE 9

Figure 12:
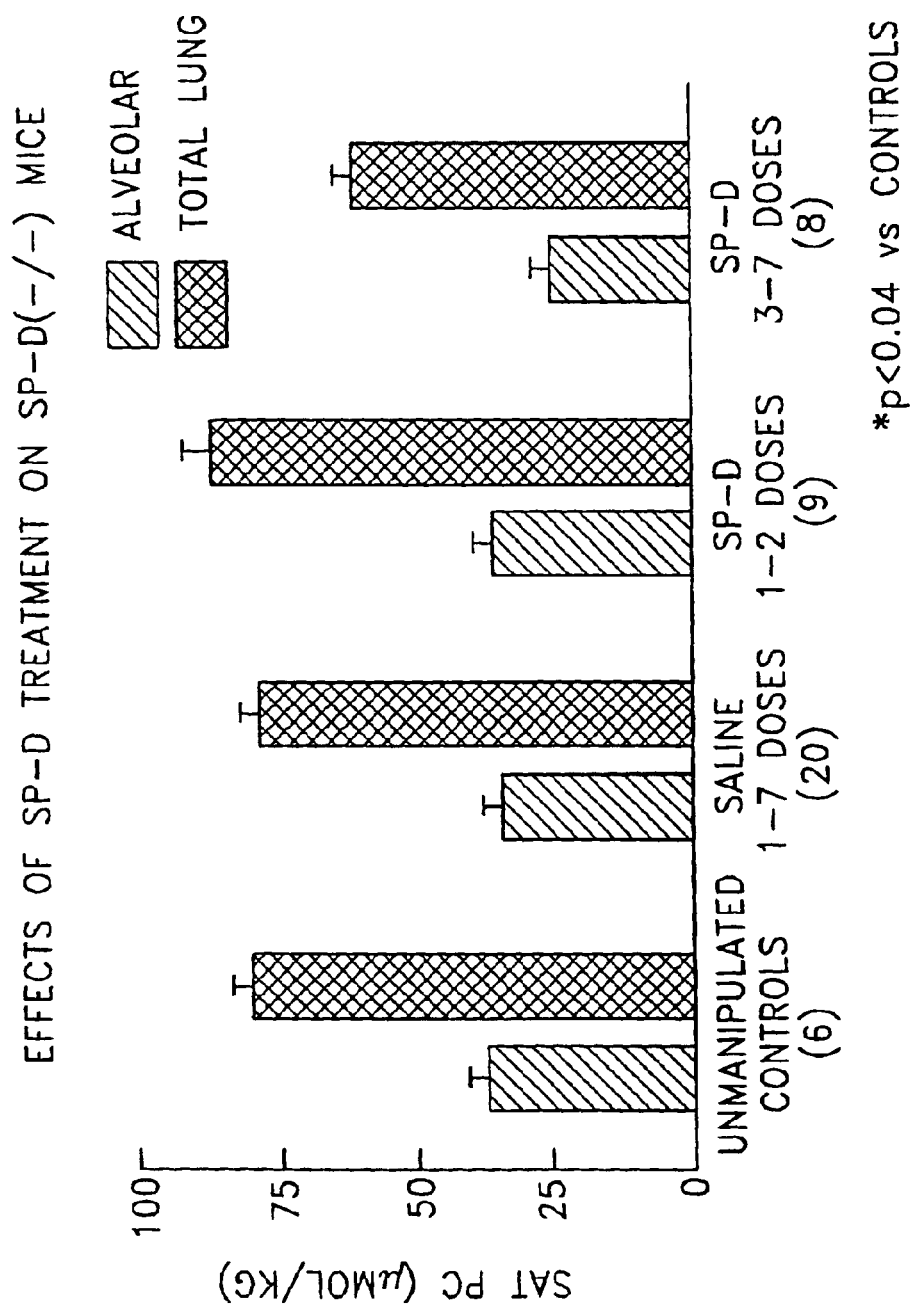
FIG. 12: Effects of SP-D protein treatment on SP-D (−/−) mice.

SP-D(−/−) mice were treated with purified mouse SP-D, purified as outlined below. Saturated PC levels were analyzed in alveolar lavage and total lung lavage. Repeated doses intratracheally at 24 hour intervals resulted in partial correction of lipid accumulation after 3 to 7 doses, see FIG. 12.

Figure 13A:
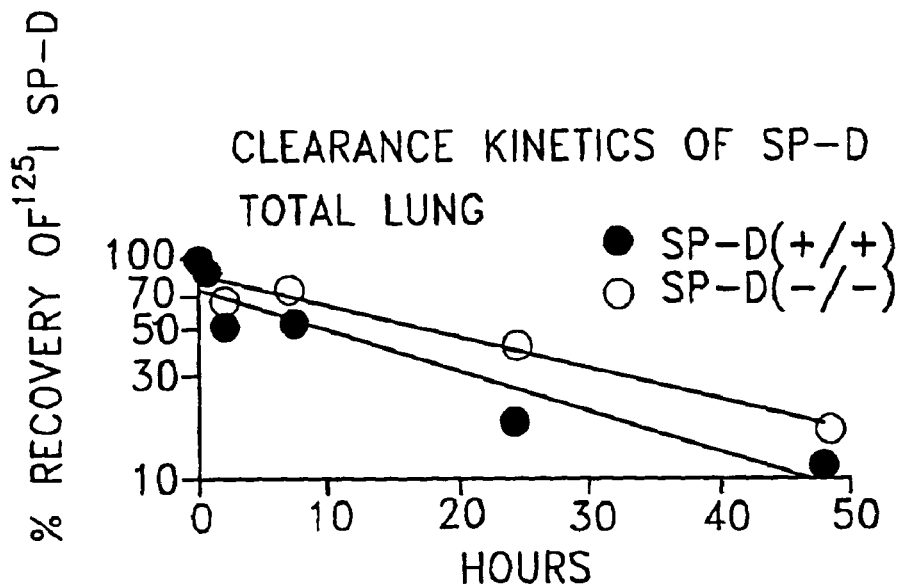
FIG. 13: Total lung and alveolar lavage clearance kinetics of SP-D protein in mice.
Figure 13B:
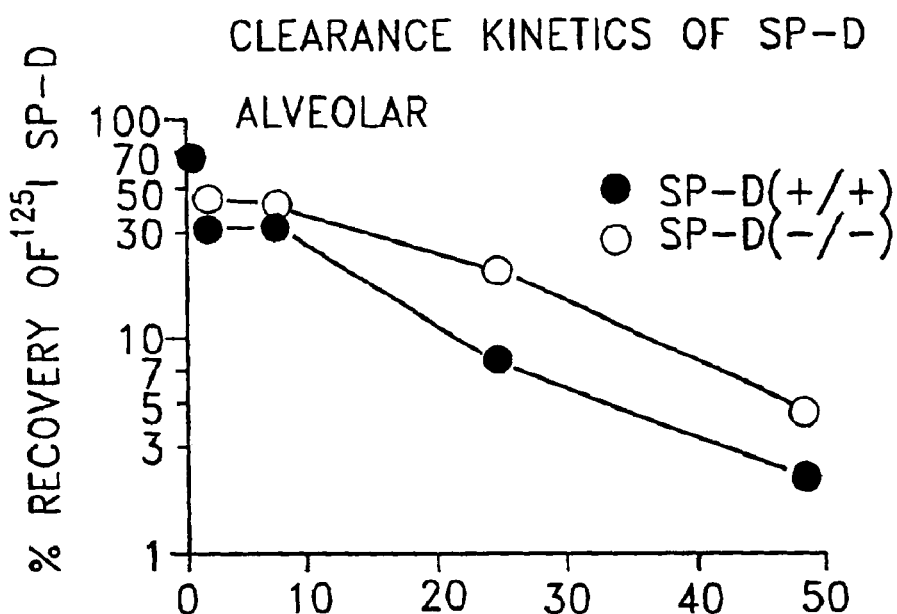

The half life of SP-D in the airway was determined as 13 hours in mouse (see FIG. 13) (the technique is outlined below); therefore, the SP-D deficiency can be treated by replacement of SP-D protein at a reasonable interval by aerosol or particulate inhaler or surfactant mixtures.

Purification of Mouse SP-D

Mouse bronchoalveolar lavage (BAL) fluid from GMCSF and SP-A double null mutant mice was collected, frozen, and pooled for later purification of SP-D. Maltosyl-agarose (Sigma) was packed in a gravity flow column (10×80 mm) and equilibrated with buffer containing 20 mM Tris-HCl, pH 7.4, 10 mM calcium chloride, 0.02% (W/V) sodium azide (TCB). The BAL was made 20 mM with respect to Tris-HCl, and 10 mM with respect to EDTA, ph 7.4 and stirred for one hour at room temperature. The turbid solution was centrifuged at 10,000×g for 40 minutes at 4 degrees C. The supernatant was made 20 mM with respect to calcium chloride and readjusted to pH 7.4 before loading on the maltosyl-agarose column. The column was washed to background absorbence with TCB followed by washing with TCB containing 1.0 M Sodium Chloride. The SP-D, which has a specific requirement for calcium in binding to maltose was eluted with 50 mM manganese chloride, 20 mM Tris-HCl, 0.02% (W/V) sodium azide, pH 7.4. The fractions containing SP-D were determined by SDS polyacrylamide gel electrophoresis or by direct ELISA, pooled, and dialysed against three changes of 20 mM Tris-HCl, 100 mM sodium Chloride, 5 mM EDTA pH 7.4. This protocol was adapted from Strong, Peter; Kishore, Uday; Morgan, Cliff; Bernal, Andres Lopez; Singh, Mamta; and Reid, Kenneth B. M.; Journal of Immunological Methods 220 (1998) 139–149.

Treatment of Mice with Surfactant Components

We have successfully used a technique for oral blind intubation using 26 g feeding tubes in mice under anesthesia with isoflurane for repetitively treating mice with SP-D daily for up to 7 days without problems. This approach avoids surgery and permits the type of experiments proposed for SP-D replacement and treatment with mutant SP-D proteins.

Initially SP-D(−/−) mice were treated with purified mouse SP-D by tracheal instillation. Three or more doses of 2.9 μg SP-D given at 24 hour intervals decreased both alveolar and saturated PC pools (see FIG. 14). This dose of SP-D given is approximately the amount present in the endogenous pool in SP-D(+/+) mice. Given the lung association and clearance kinetics, this is a low dose. Thus exogenous administration of SP-D directly influences surfactant lipid metabolism and provides an experimental model in which we can test the function of modified SP-D molecules in vivo.

Biological Half-life Protocol

We have measured the biological half-life of SP-D in mice in order to design experiments for treatment with SP-D. We iodinated purified mouse SP-D with $^{125}$I using the Bolton-Hunter reagent as we have done previously for SP-A and the other surfactant proteins. The clearance of SP-D from alveolar lavages of SP-D(+/+) and SP-D (−/−) mice was similar with a half life of about 13 hours (see FIG. 13). The $t^{1/2}$ of 17 h for SP-D in the lungs of SP-D(−/−) mice was somewhat longer than the $t^{1/2}$ of 13 hours for SP-D(+/+) mice.

GM-CSF deficiency causes a 48 fold increase in SP-D, and the GM-CSF (−/−)×SP-A(−/−) cross has similarly elevated SP-D but no SP-A. We have isolated SP-D from alveolar washes from GM-CSF(−/−)×SP-A (−/−) mice in high purity and in large amounts by the methods described by Persson et al. using an affinity column of mannose-Sepharose 6B in the presence of Ca2+.

EXAMPLE 10

Treatment with SP-D Expressed from an Adenovirus

We made a new adenovirus expressing rat SP-D. The virus produces SP-D in cells and in the lungs of normal or SP-D deficient mice. We have Western blots of the rat SP-D produced in 293 cells and in mice.

Figure 14:
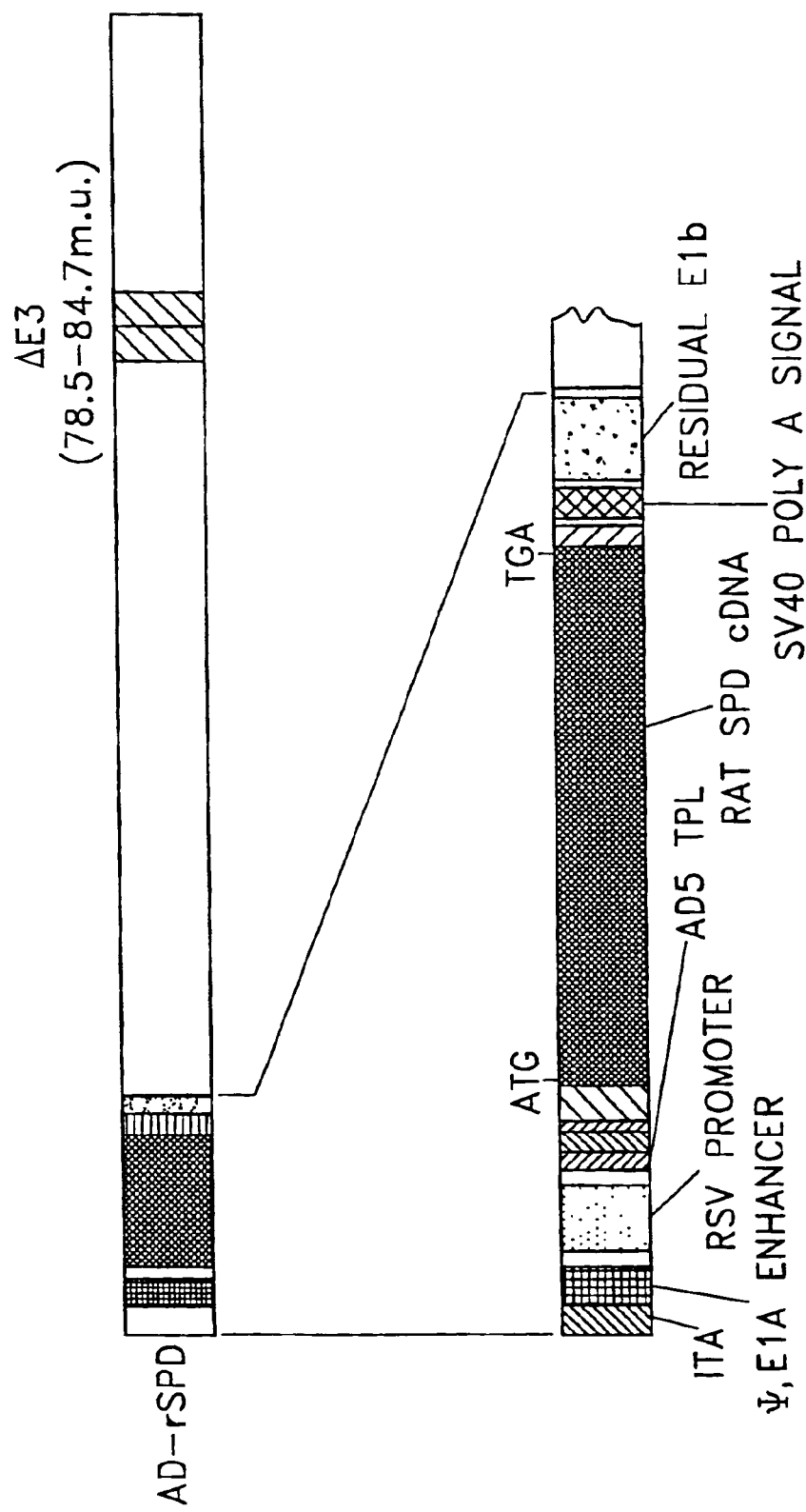
FIG. 14: Adenoviral vector Ad-rSPD containing rat SP-D cDNA.

Construction of Ad-rSPD Adenovirus (see FIG. 14)

Wild type rat SPD cDNA was liberated from plasmid WT-rSPD/pG3Z with EcoR I digestion and the 3' ends filled in with Klenow. The 1.3 kB rSPD cDNA was inserted into the EcoR V site of plasmid pAvS6a to make plasmid pAvS6a-rSPD. Plasmid pAvS6a-rSPD has a RSV promoter, a rSPC cDNA, an SV40 poly A signal and an Ad5 sequence (9.24–17.34 mu). Not I linearized pAvS6a-rSPD was co-transfected into 293 cells with Cla I digested large fragment of adenovirual DNA Ad dl327, which has E3 region (78.5–84.7 mu) deleted. After homologous recombination, individual plaques were analyzed by Western blot assay to determine rSPD protein expression. One rSPD positive clone was subject to one round of plaque purification. The Ad-rSPD adenovirus has deletions in E1 and E3 regions and is replication deficient. After amplification in 293 cells, the purified Ad-rSPD adenovirus was produced through two rounds of CsCl gradient ultracentrifugation. The adenovirus expressed SP-D and therefore could be used to restore pulmonary abnormalites by intratracheal administration. Therefore, this remains a very positive possibility for treatment of emphysema and many other SP-D deficiency illnesses as well as various other forms of pulmonary injury and deficiency.

EXAMPLE 11

Treatment with SP-D Expressed from other Vectors, Proteins, or Pharmaceuticals

The temporal, spatial and stoichiometric requirements for SP-D in the restoration of phospholipid homeostasis were determined in example 9. Initial studies to determine the kinetics of clearance of SP-D were performed with $^{125}$I labeled SP-D administered intratracheally; half-life was calculated and the information used in design of SP-D replacement experiments. The dose of SP-D required to achieve normal physiologic concentrations of SP-D after administration was clarified.

Administration of purified SP-D protein was used to treat various pulmonary disease in Example 9. However, physiologic abnormalities in pulmonary disease may require long term correction of SP-D in the lungs. Therefore, recombinant adenovirus or other genetic vectors containing the mammalian SP-D gene will be used (see Example 10 and 11). Recombinant adenovirus vectors or Clara cell secretory protein (CCSP) and SP-C promoters can be used to selectively express SP-D in bronchiolar (Clara cell) and alveolar (Type II cell) compartments (see Example 10). Three days prior to treatment with adenoviral vector the mice are immunosuppressed by injection intraperitoneally with 200 ug of monoclonal anti-T cell receptor antibody, H57. Adenovirus was administered by intratracheal injection of $5 \times 10^8$ PFU of virus. Levels of SP-D protein were measured 1 week after administration to detect uptake and expression of the vector. Four mice were tested and SP-D (−/−) mice receiving no treatment are used as a control. To test for efficacy of the SP-D at diminishing the effects of emphysema, a number of tests are performed as follows.

To determine the effects of a protein or pharmaceutical on the lung structure (Example 11), lungs are inflation fixed and sections evaluated by electron microscopy. Lungs are inflated via a tracheal cannula at 20 cm of pressure with 4% paraformaldehyde and removed en bloc from the thorax. Lungs are dehydrated and embedded in paraffin. Tissue sections (5 μm) are stained with hematoxylin and eosin.

Number and morphology of macrophages are analyzed. Staining with Nile Red detects vesicles and staining with Nile Blue and exciting with 520–550 mm green light is an additional method to detect lipid or phospholipid. Macrophage number is determined by direct counting or macrophage cell surface markers. Macrophage size is estimated from the diameter of fixed and stained macrophages from cytospin preparations sedimented onto glass slides at 1500×g for 2 min.

Surfactant composition and ultrastructure are analyzed as follows: the structure of surfactant is analyzed by isolating large aggregates from pooled alveolar lavage of SP-D (−/−) treated and untreated mice and examined by EM. For alveolar lavage phospholipid composition analysis, two to four samples consisting of the pooled lavage from two to three mice are evaluated for the relative abundance of phosphatidylcholine, phosphatidylethanolamine, phosphatidylglycerol, phosphatidylinositol, sphingomyelin, and lyso-bis-phosphatidic acid. Incorporation of ($^3$H)choline into total lung Sat-PC is evaluated to determine total phospholipid concentration.

Once efficacy of the treatment is determined, treatment can be tested on other appropriate mammals.

Involvement of SP-D in Pulmonary Infection

The role of SP-D and SP-A in host defense in the lungs has been repeatedly demonstrated. SP-A and SP-D have specific interactions with various microorganisms in vitro, modifying pulmonary inflammation in vitro by altering cytokine and free radical production. The role of SP-D in bacterial clearance and inflammatory response of the lung was evaluated in vivo using a mouse model of SP-D deficiency. SP-A-deficient mice are known to be more susceptible to infections. A number of in vitro studies have shown a possible role for SP-D in host defense in addition to its role in up-regulating SP-A. Examples 8–11 outline sample protocols for testing SP-D as a therapy in the, bacterially, or fungally infected SP-D (−/−) mice as well as in the SP-A (−/−) mice. Examples 12–14 are experiments showing the role of SP-D in the response to bacterial, fungal, and viral infection. Example 13 is an experiment showing the effect of infecting SP-D(−/−) mice with Respiratory Syncytial Virus.

EXAMPLE 12

Clearance of Bacterial Agents from SP-D(−/−) Mice

Figure 8A:
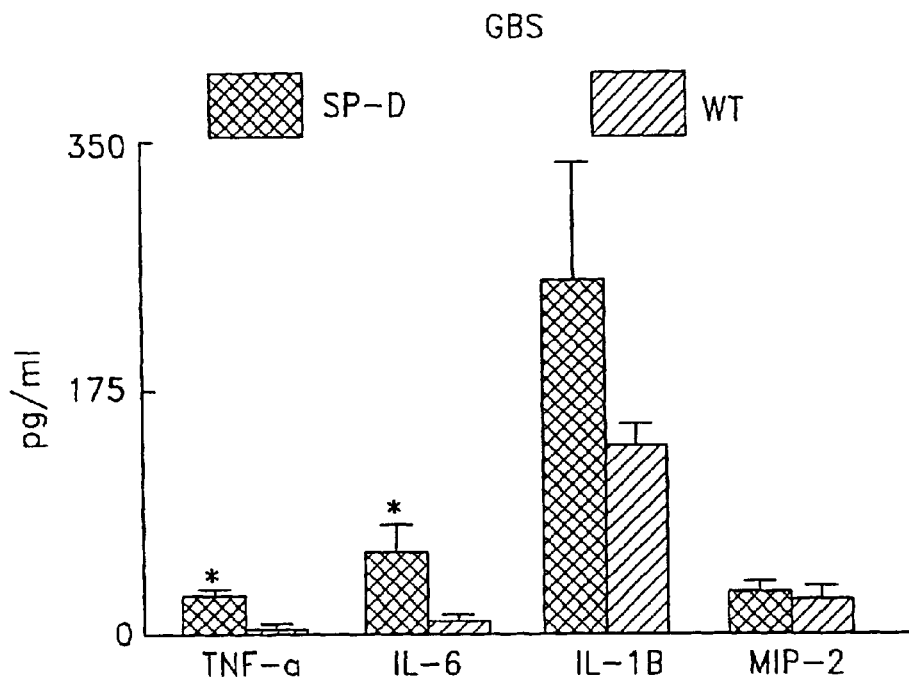
FIG. 8: Cytokine levels in lung homogenates after infection with GBS and H. flu.
Figure 8B:
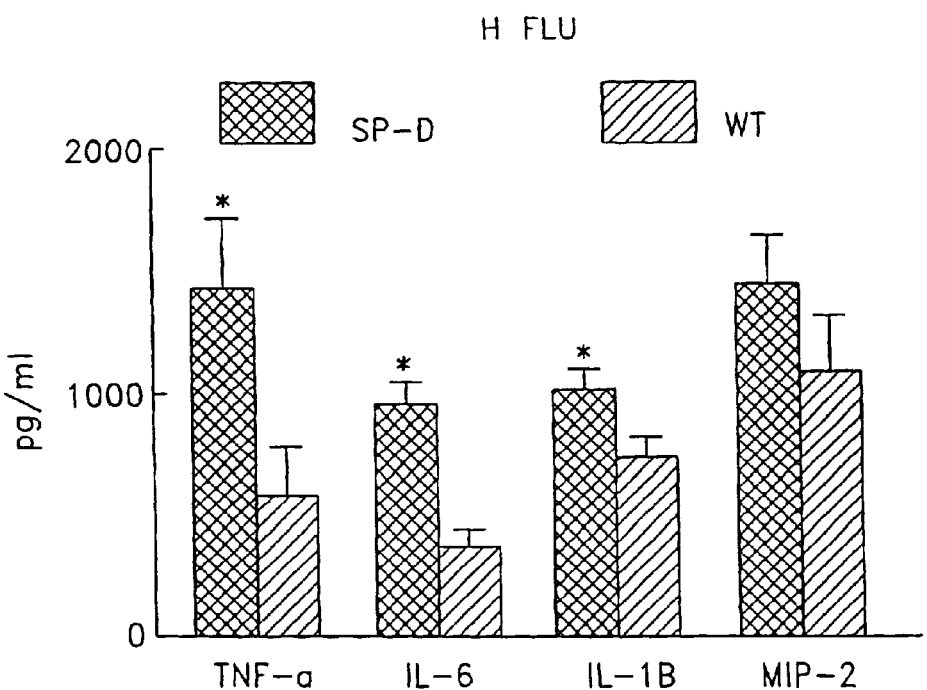
Figure 9A:
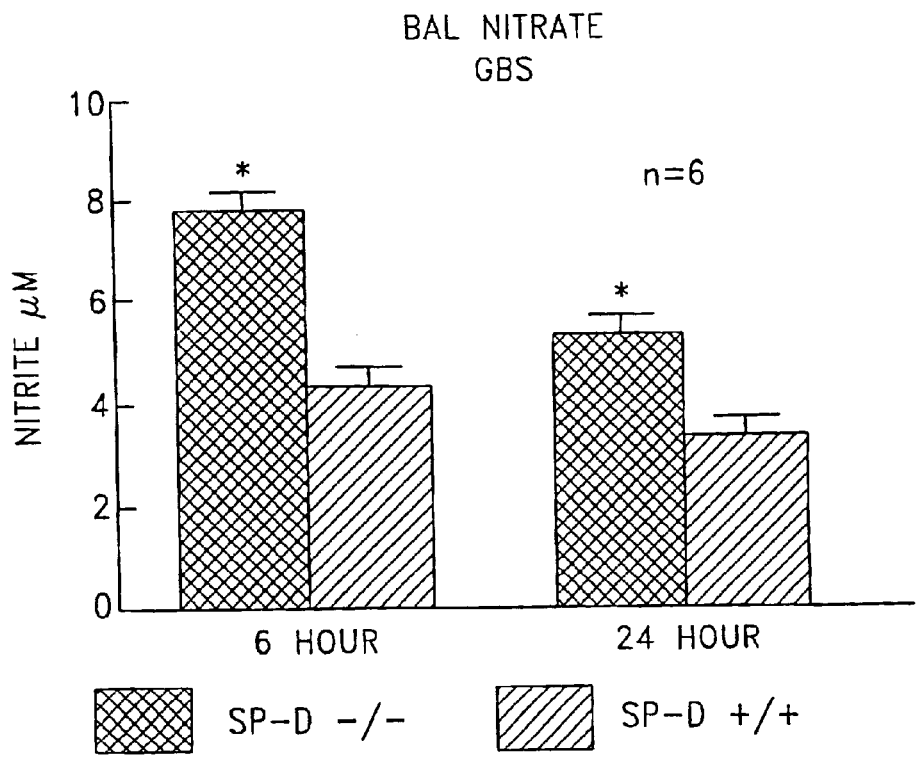
FIG. 9: BAL nitrite levels after infection with GBS and H. flu.
Figure 9B:
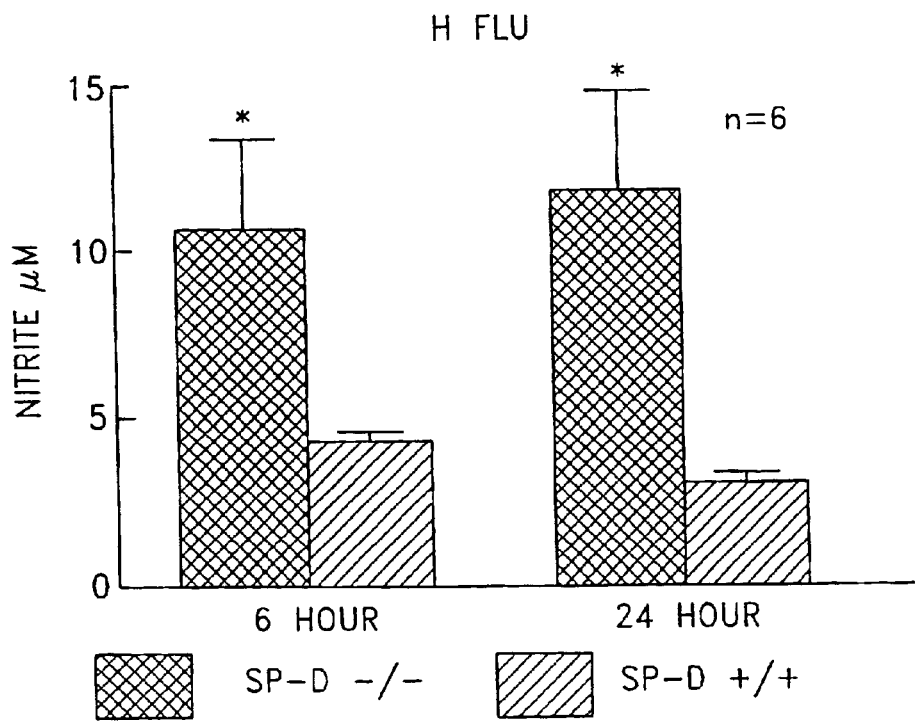

SP-D deficient mice (SP-D −/−) were intratracheally infected with Group B streptococcus (GBS) or *Hemophilus influenzae* (Hflu) to assess clearance compared to wild type mice. Group B Streptococcus was administered at $10^4$ CFU. Pulmonary inflammation was also assessed by analysis of BAL fluid for total cells (FIGS. 5, 6, and 7), cytokine levels in lung homogenates (FIG. 8), oxygen radical production by alveolar macrophages (FIG. 11) and nitrite levels in BAL (FIG. 9).

Figure 5:
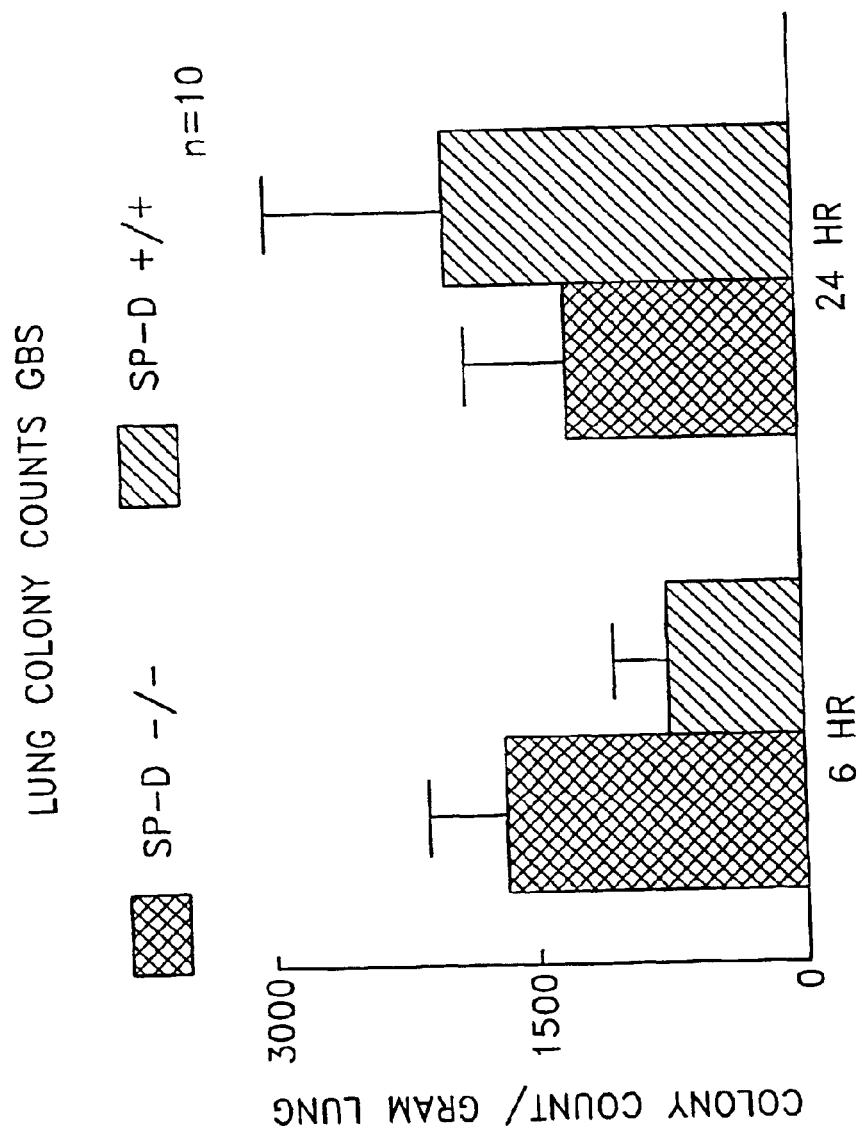
FIG. 5: Lung colony counts in SP-D(−/−) and SP-D(+/+) mice after infection with Gp B Streptococcus (GBS).
Figure 6:
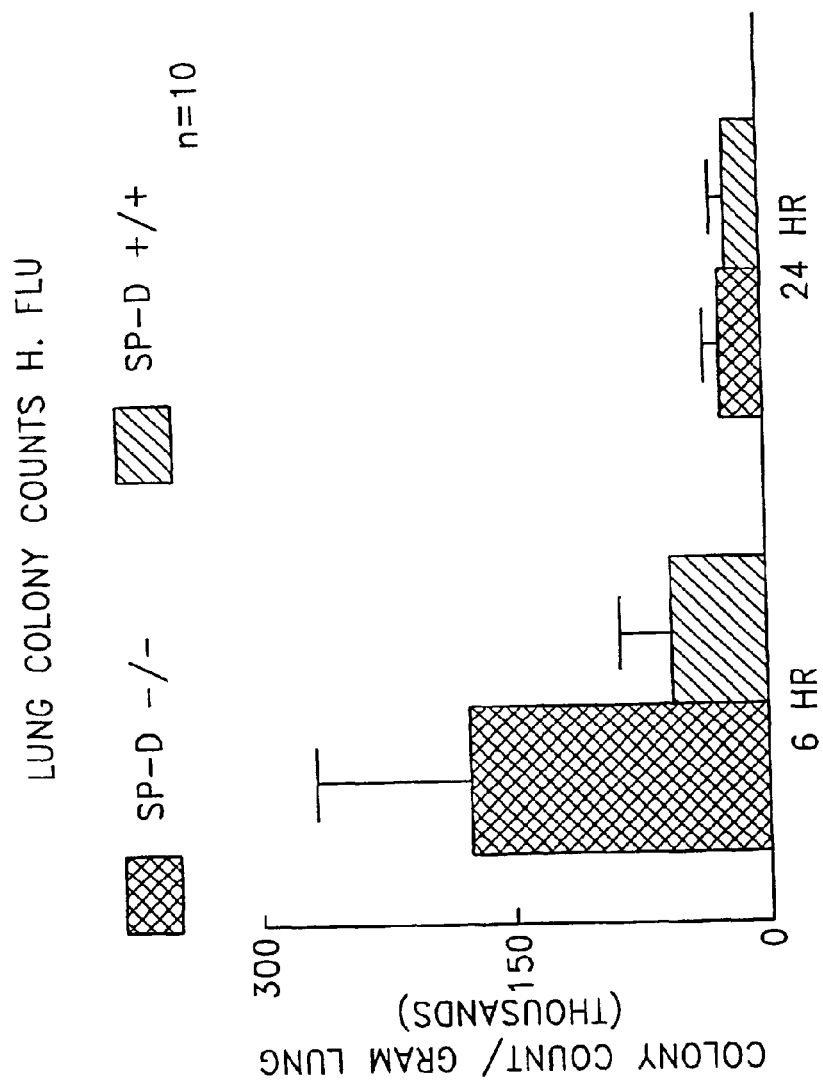
FIG. 6: Lung colony counts in SP-D(−/−) and SP-D(+/+) mice after infection with *Haemophilus influenzae* (H.flu).
Figure 7A:
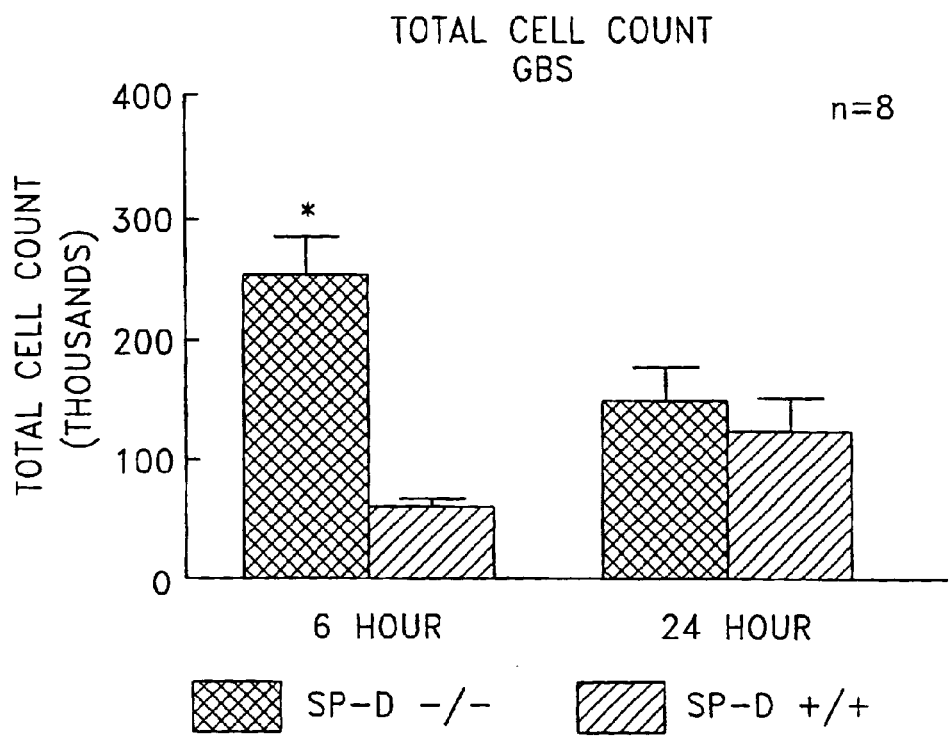
FIG. 7: Total cell count in Bronchoalveolar lavage (BAL) fluid after infection with GBS and H.flu.
Figure 7B:
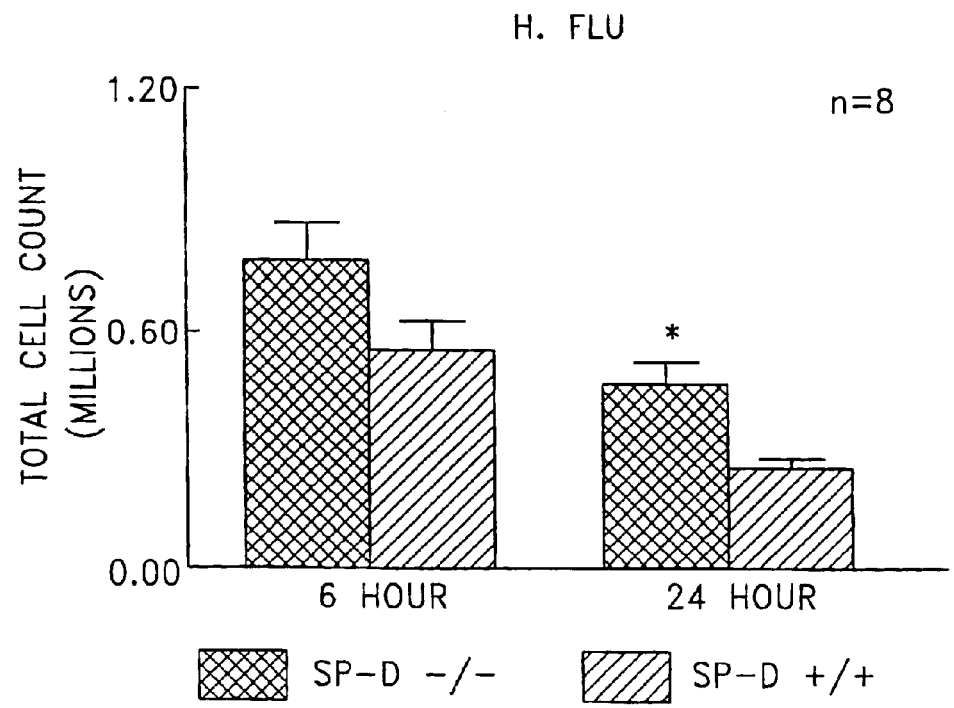
Figure 11A:
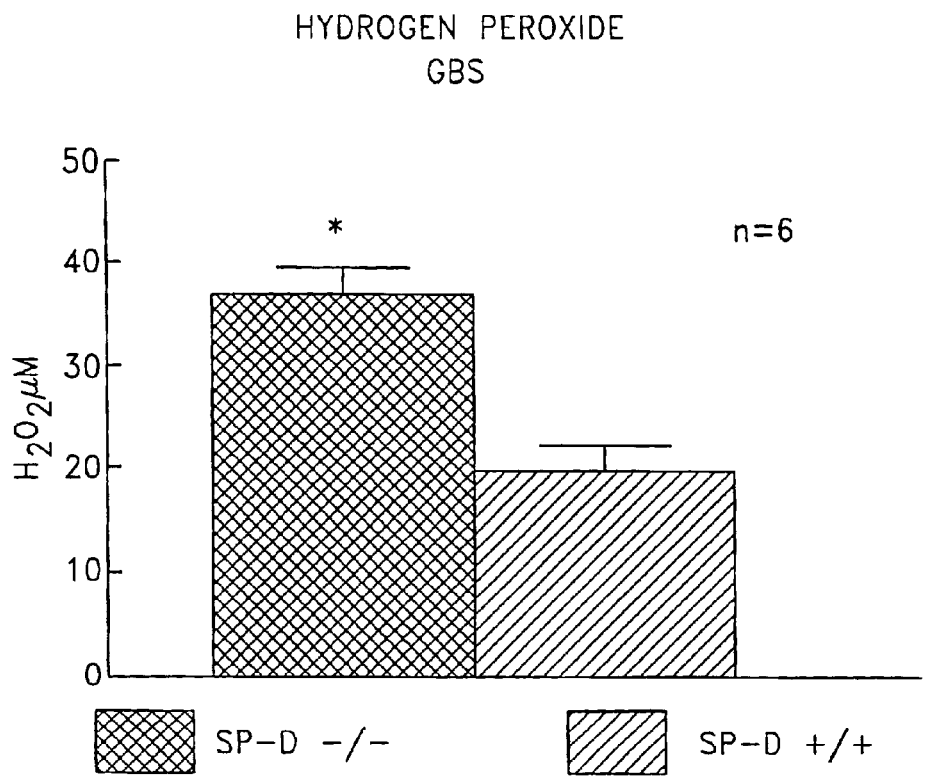
FIG. 11: Hydrogen peroxide and superoxide levels in macrophages isolated from BAL after infection with GBS and H.flu.
Figure 11B:
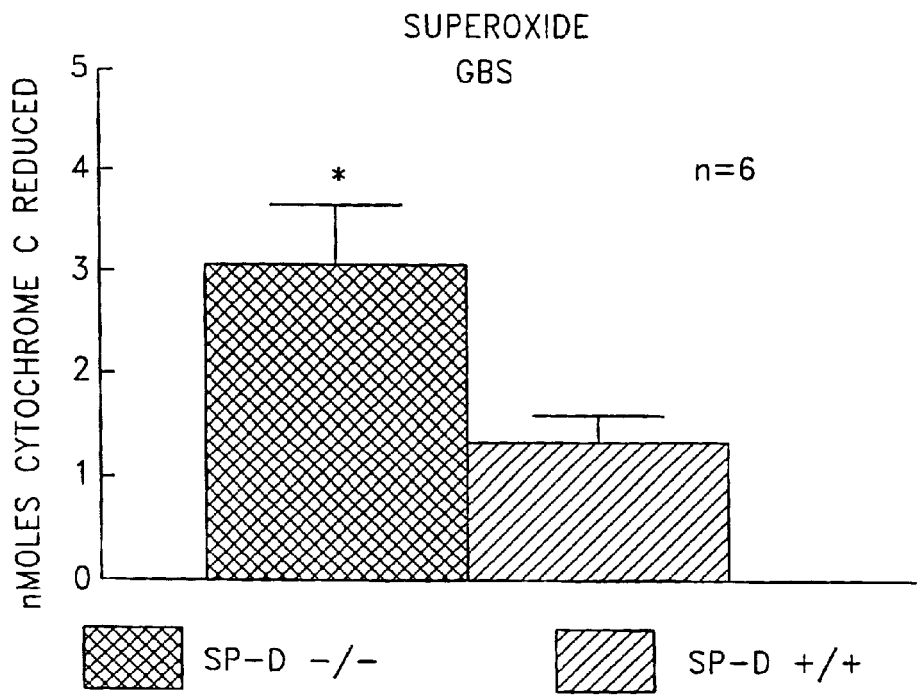

SP-D −/− mice cleared the bacteria similarly to wild type mice (see FIGS. 5 and 6). Infection with GBS and Hflu resulted in significantly greater total cells in the BAL fluid of the SP-D −/− mice compared to wild type mice (FIG. 7). Selective alterations of cytokine levels were detected in SP-D −/− mice. Tumor necrosis factor α (TNF-α) and interleukin (IL)-6 levels were greater in lung homogenates from SP-D −/− mice early after infection with GBS or Hflu (FIG. 8). Macrophage inflammatory protein-2 (MIP-2), a neutrophil chemoattractant, was significantly greater in lung homogenates from SP-A −/− mice after Hflu but not GBS infection (FIG. 8). Macrophages from SP-D −/− mice generated significantly greater superoxide and hydrogen peroxide compared to wild type mice (FIG. 11).

BAL nitrite levels were increase in SP-D (−/−) mice as compared to wildtype mice. Nitric oxide production was measured as nitrite in BALF. Nitric oxide plays a role in host defense by contributing to bacterial killing. Nitric oxide reacts with superoxide to form peroxynitrite which is a potent bacteriocidal agent.

Figure 10A:
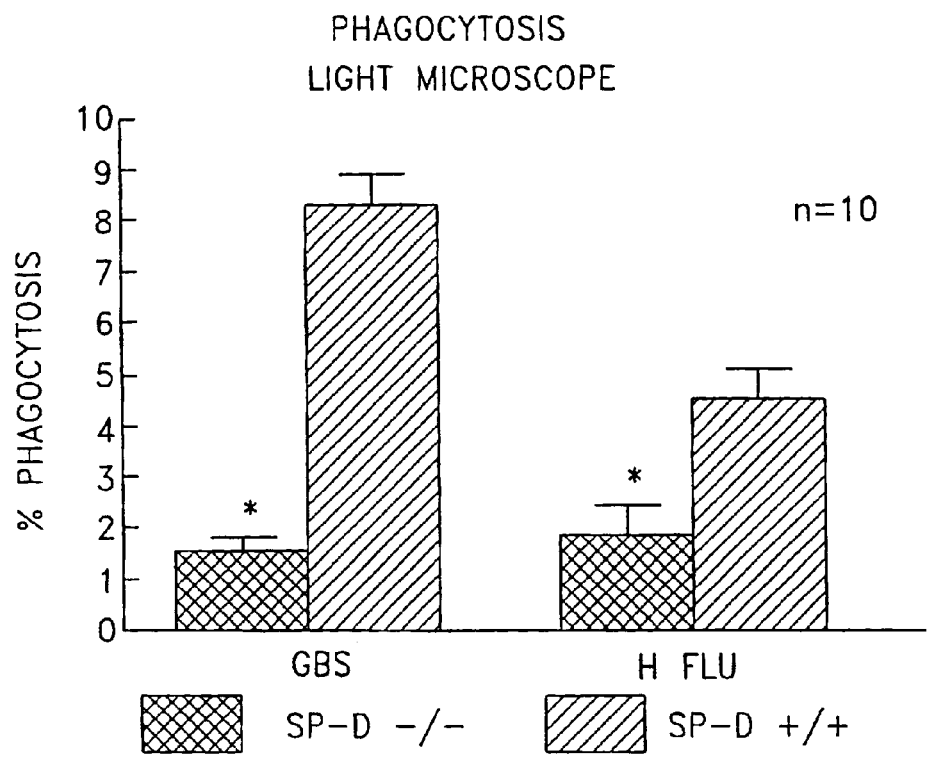
FIG. 10: Phagocytosis analyzed by light microscopy and FACS analysis after infection with GBS and H.flu.
Figure 10B:
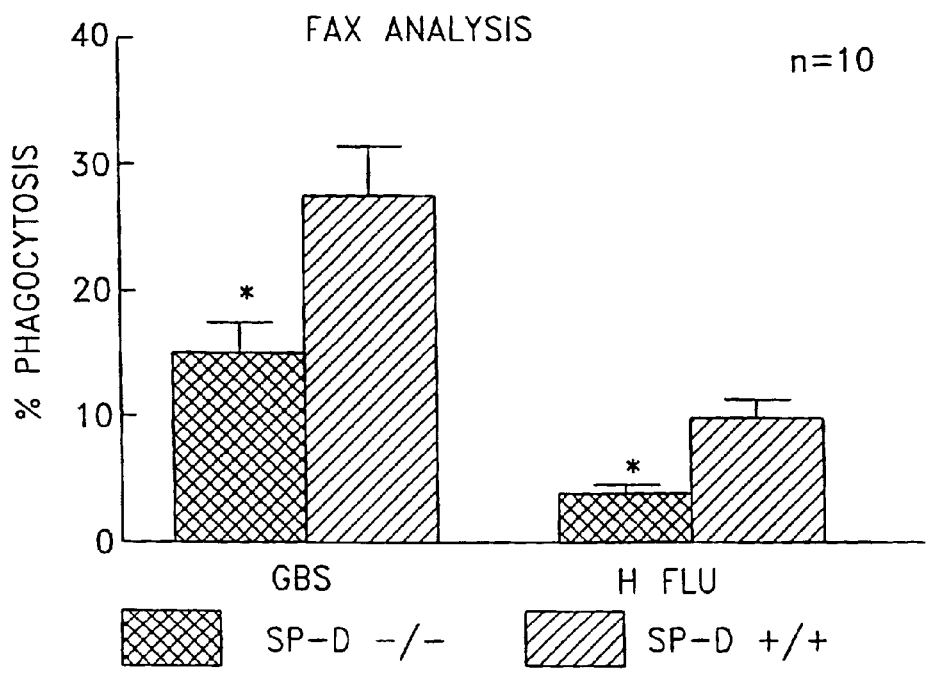

In FIG. 10 phagocytosis was evaluated using light microscopy and flow cytometry. SP-D(−/−) mice showed significantly reduced phagocytosis of bacteria as compared to wildtype.

Therefore, in the absence of SP-D increased inflammatory responses were observed following bacterial infection of the lung with GBS or Hflu. Production of reactive oxygen species by alveolar macrophages was enhanced in SP-D −/− mice. These results support a critical and distinct role of SP-D in pulmonary immune and inflammatory responses to bacterial infection, in vivo.

In Example 13, the SP-D(−/−) mice were infected with Respiratory Syncytial Virus.

Host defense mechanisms have evolved to maintain the lung clear of microbial pathogens including innate mediators of bacterial and viral clearance and acquired immune responses.

EXAMPLE 13

Clearance of Virus from SP-D(−/−) Mice

SP-D(−/−) mice were intratracheally infected with respiratory syncytial virus (RSV), a common respiratory pathogen in children. Viral titers and lung inflammation were assessed in SP-D (−/−) mice and wild type mice. RSV titers in lung homogenates were significantly increased in SP-D (−/−) compared to wild type mice 3 and 5 days after administration. However, significantly increased numbers of inflammatory cells were found in BAL fluid from SP-D (−/−) mice with a greater percentage of PMNs compared to wild type mice, 3 and 5 days after RSV infection. In addition, lung inflammation assessed by histology, 5 days after RSV infection was greater in SP-D (−/−) compared to wild type mice. Pro-inflammatory cytokines, including TNF-a, IL-1, IL-6 and MIP-2 were greater in lung homogenates from SP-D (−/−) mice 3 and 5 days after RSV infection. SP-D (−/−) mice had less efficient viral clearance from the lung and demonstrated greater inflammatory responses following RSV infection than wild type mice. These findings demonstrate that SP-D plays an important role in innate defense and regulation of inflammation in the lung after RSV infection in vivo. Similar findings were observed after Influenza and adenovirus infected the lung.

EXAMPLE 14

Clearance of Fungi from the SP-D(−/−) Mice

The mouse is infected as follows: an appropriate prototype of a fungal pathogen is used. The infectious agent is purified as appropriate and suspended in appropriate buffer and administered intratracheally with or without SP-D into the SP-D (−/−) mouse (as in Examples 12 and 13). The fungal prototype is administered at an appropriate dose. SP-D (−/−) and SP-D (+/+) mice are used to test the effect of SP-D on susceptibility of mice to infection. SP-D (−/−) mice with or without SP-D protein is used to test SP-D as a therapy for infection. Clearance of infection is evaluated as in Examples 12 and 13 and as follows:

Fungal clearance is determined by purifying lung and spleen homogenates at 6, 24, and 48 hours after inoculation of the animals with infectious agent or infectious agent with SP-D. Bacterial clearance from the lungs is determined after varying SP-D concentrations appropriately. Quantitative cultures are also determined for the SP-D (+/−) mice a to determine if 50% reduction in SP-D provides sufficient endogenous SP-D for bacterial or viral clearance.

Appropriate concentrations of mammalian SP-D are used in other mammals for treatment of pulmonary infections.

Pharmaceuticals that Regulate SP-D Levels

The importance of SP-D in normal function and development of the lung is clearly demonstrated by the SP-D (−/−) null mouse. Therefore, agents that regulate production, expression, or the action of SP-D are important future pharmaceuticals and experimental aids for identifying further such pharmaceuticals. Many techniques for identifying such agents would suggest themselves to one having ordinary skill in the art. Examples 15 and 16 outline a sample protocol for two of these techniques. Example 17 shows that IL-4 markedly increases SP-D levels in vivo and could thus be used to treat various pulmonary diseases with or without the addition of SP-D.

EXAMPLE 15

Proteins that Interact with the SP-D Promoter

A one-hybrid technique is set up using the SP-D promoter to identify proteins that up-regulate expression of SP-D. These proteins are then tested on the SP-D (−/−) mouse for efficacy in treating emphysema and other pulmonary diseases and infections as in Example 8.

EXAMPLE 16

Proteins that Interact Directly with the SP-D Protein

A two-hybrid technique is set up to identify proteins that interact directly with the SP-D protein. These proteins are then be tested on the SP-D (−/−) mouse for efficacy in treating emphysema and other pulmonary diseases and infections as in Example 8.

EXAMPLE 17

IL-4 Increases SP-D Levels in vivo

Figure 15:
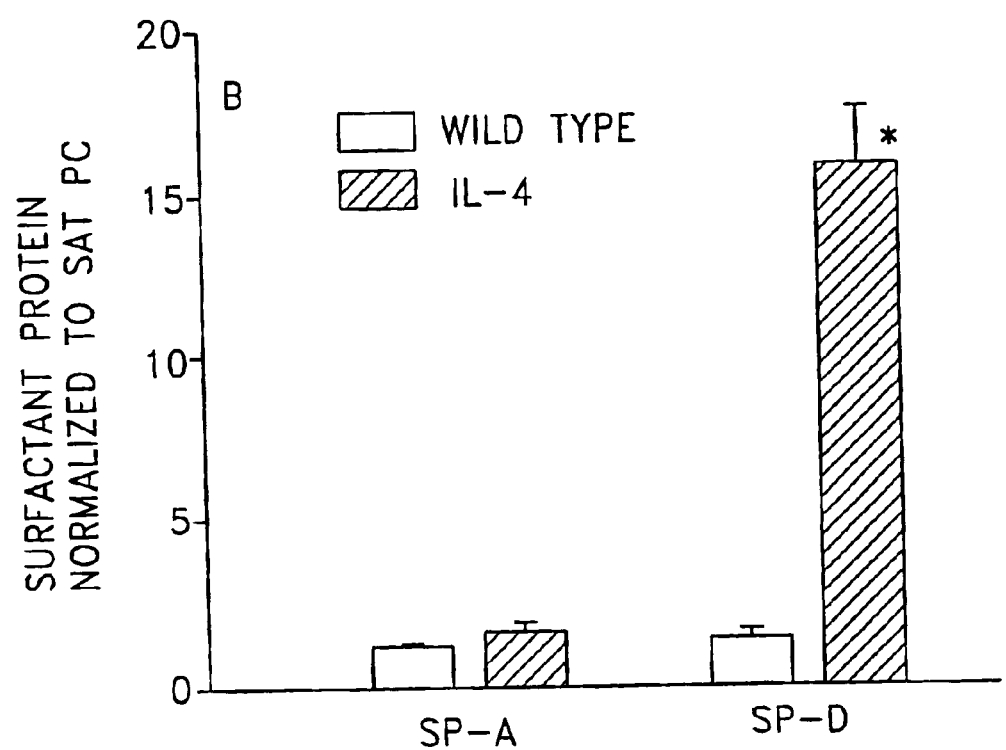
FIG. 15: Quantification of immunoblots of SP-A and SP-D in alveolar washes from wild type and CCSP-IL-4 mice (IL-4 mice). p<0.01.
Figure 17A:
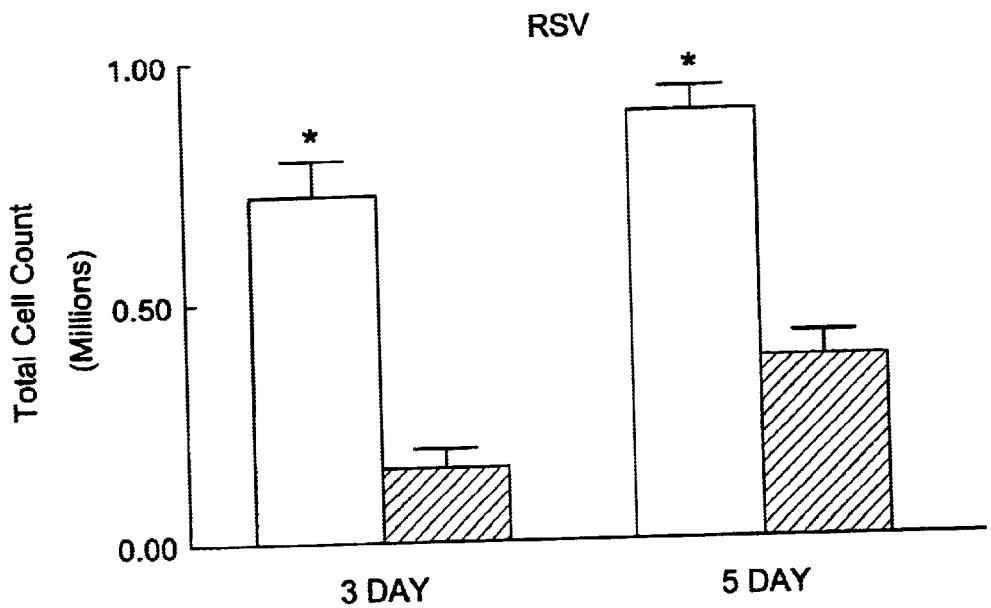
FIG. 17: Lung cells were recovered by bonchoalveolar lavage, stained with trypan blue and counted under light microscopy. SP-D −/− mice (open bar) had increased total cell counts in BAL fluid 3 and 5 days after RSV infection (graph A) compared to wild type mice (hatched bar). SP-D −/− (open bar) had increased total cell counts in BAL fluid 3 and 5 days after IAV infection (graph B). Data are mean±SEM with n=8 mice per group, *p<0.05 compared to wild type mice.
Figure 17B:
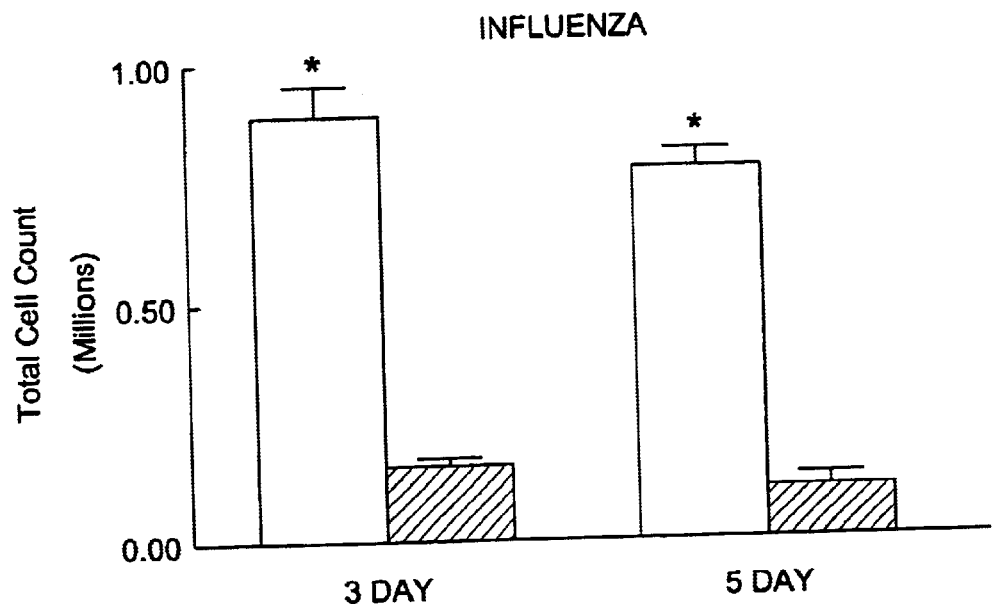
Figure 18A:
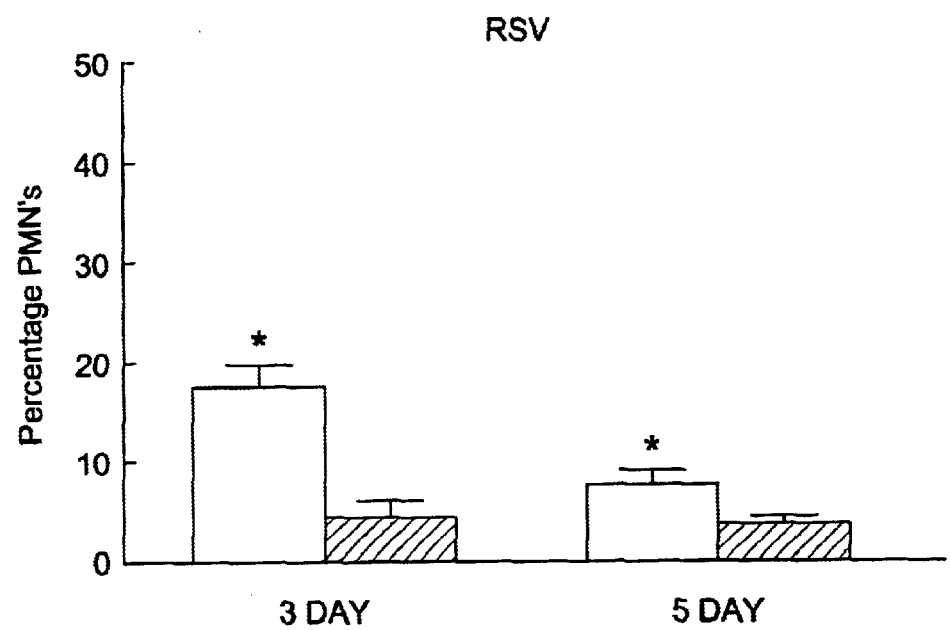
FIG. 18: Cytospin preparations of bonchoalveolar lavage fluid were stained with DIFF-QUIK to identify macrophages, lymphocytes and polymorphonuclear leukocytes. The percentage of neutrophils in BAL fluid was significantly greater 3 and 5 days after administration of $10^7$ pfu RSV to SP-D −/− (open bar) compared to wild type (hatched bar) mice (Graph A). Similarly, the percentage of neutrophils in BAL fluid was significantly greater 3 and 5 days after administration of $10^5$ pfu IAV to SP-D −/− (open bar) mice compared to wild type (Graph B). Data are mean±SEM with n=8 mice per group, *p<0.05 compared to wild type mice.
Figure 18B:
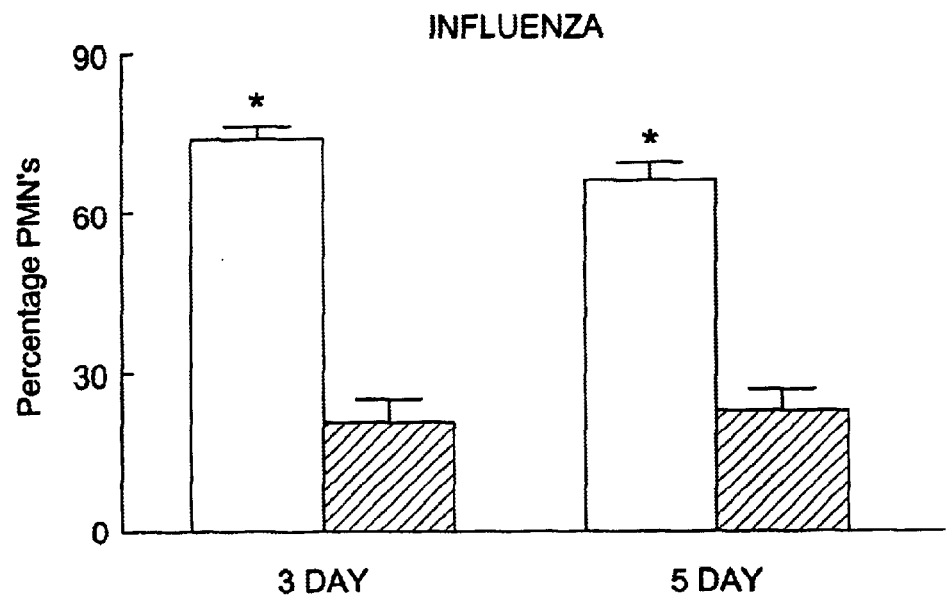

Mice that express IL-4 in Clara cells (CCSP-IL-4) develop chronic airway inflammation and an alveolar proteinosis-like syndrome. In order to identify the role of IL-4 in surfactant homeostasis, we measured lipid and protein metabolism in the lungs of CCSP-IL-4 mice in vivo. Alveolar saturated phosphatidylcholine (Sat PC) pools were increased 6.5 fold and lung tissue Sat PC pools were increased 4.8 fold in the IL-4 transgenic mice (see FIG. 15). SP-D was increased approximately 90 fold in the IL-4 mice compared to wild type mice and was associated with 2.8 fold increased SP-D mRNA (see FIG. 15). The incorporation of palmitate and choline into Sat PC was increased about 2 fold in CCSP-IL-4 mice. Net clearance of Sat PC from the lungs of CCSP-IL-4 mice was 6 fold higher (60 $\mu$mol/kg) in the IL-4 mice than in wild type mice (10.3 $\mu$mol/kg). Expression of IL-4 in Clara cells increased surfactant lipid synthesis and clearance, establishing a new equilibrium with increased surfactant pools and an alveolar proteinosis associated with a selective increase in SP-D protein, demonstrating a previously unexpected effect of IL-4 in pulmonary surfactant homeostasis and the regulation of SP-D levels by IL-4.

Diagnosis Using SP-D Protein or Sequence

SP-D is important in normal lung function and development. SP-D (−/−) mice are a model for emphysema. This then suggests that mutations in the gene or alleles of the gene for SP-D have a profound effect on pulmonary disease susceptibility. Therefore, a method to identify mutations or alleles, and mutant protein identifies individuals at risk for emphysema, pulmonary infections, and a number of other respiratory diseases. Example 18 and 19 are sample protocols for these diagnostic techniques.

Diagnosis of Patients with Mutations in the SP-D gene

EXAMPLE 18

Mutations in the SP-D gene are likely involved in the symptoms and etiology of emphysema. Therefore, mutations are identified by sequence analysis of a statistically significant number of patients. These mutations are used to produce a diagnostic test. Mutations in the SP-D gene are detected in the following ways: PCR analysis of the SP-D gene using appropriate primers is performed. Resulting PCR fragments are analyzed by SSCP and sequenced to determine mutation or allele. Alternatively, differential hybridization of genomic DNA or cDNA is used to detect mutations.

Diagnosis of Patients with Mutant SP-D Protein

EXAMPLE 19

Monoclonal or polyclonal antibodies which specifically recognize mutant SP-D protein or an allele of SP-D associated with emphysema or other pulmonary diseases are produced. These antibodies are then used to set up an enzyme-linked immunoassay or Western blot assay for susceptibility to these pulmonary diseases. The antibodies of Example 20 can be used for this assay.

Example 20 presents a protocol for the purification of polyclonal or further purification of monoclonal antibodies using transgenic technology.

EXAMPLE 20

Purification of SP-D Specific Monoclonal and Polyclonal Antibodies

The production of specific polyclonal antibodies with a high reactivity requires extensive purification of the antigen of interest. We have developed several polyclonal antibodies using partially purified antigens for injection which have resulted in antibodies which have a high titer with respect to the antigen of interest and are also reactive to impurities. Solid phase tissue from transgenic mice have been used to remove nonspecific antibodies from these antisera. Surfactant Protein-D (SP-D) was purified using a maltose column with manganese elution. The purified SP-D was injected into New Zealand rabbits in incomplete Freund's adjuvant. The resulting antisera was tested against whole lung lavage on a Western Blot, revealing binding to the SP-D and to other proteins. This antisera was reacted overnight with a solid phased lung homogenate from a null mutant mouse which does not produce any SP-D protein. The antisera was reacted against whole lung lavage after absorption showing reactivities only against SP-D. This antisera was also evaluated in immunohistochemistry experiments which demonstrated very low reactivities to lung sections from SP-D null mutant mice and very specific type II cell reactivities in normal control mice. This technique greatly enhances the ability to prepare highly specific antibodies with high titers and eliminates the need to use blocking agents when using absorbed antibodies.

These antibodies could be used for the diagnosis, purification, and further research into the SP-D protein.

EXAMPLE 21

SP-D Inhibits Viral Infection

Previous results (Example 13) showed that SP-D has a role in the clearance of RSV from the lungs of mice. Therefore, it was of interest to see if SP-D had a similar role in the clearance of other viruses.

SP-D(−/−) mice were intratracheally infected with influenza A virus and separately with adenovirus. Viral titers and lung inflammation were assessed in SP-D (−/−) mice and wild type mice. Influenza A titers in lung homogenates were significantly increased in SP-D (−/−) compared to wild type mice 3 and 5 days after administration. Significantly increased numbers of inflammatory cells were found in BAL fluid from SP-D (−/−) mice with a greater percentage of PMNs compared to wild type mice, after Influenza A infection.

Therefore, SP-D deficient mice are susceptible to influenza A viral infection in vivo and developing markedly increased lung inflammatory responses to the virus and SP-D binds adenovirus in vitro and will likely play a role in clearance of adenovirus in vivo as well.

EXAMPLE 22

SP-D Inhibits Reactive Lipid Species

SP-D deficient surfactant has increased oxygen-lipid intermediates (toxic lipid reactants). Thus, SP-D inhibits reactive lipid species in the airspace and may have potential benefits for amelioration of reactive oxygen mediated disease, chemically induced lung injury, oxygen, ozone, chemotherapeutic agents and inflammatory diseases, reperfusion injury, drowning, transplantation, and rejection.

Reactive oxygen species were measured by the Lipid Hydroperoxide (LPO) assay kit (Caymen chemicals, Cat. No. 705002). Surfactant was isolated from SP-D knockout and wildtype mice by lung lavage and the lipid peroxidation products measured using redox reactions with ferrous ions. No lipid peroxides were detected in surfactant from wild type mice (n=4) but were readily detected in lavage fluid from SP-D (−/−) mice, 0.896±0.305 ng of lipid peroxidation product /mg of phospholipid (n=4).

What is claimed is:

1. A method for the treatment of pulmonary disease comprising: introducing a composition consisting essentially of mammalian surfactant protein-D (SP-D) protein into a human in an amount effective to reduce the symptoms of pulmonary disease.

2. The method of claim 1 wherein the pulmonary disease is selected from the group consisting of: emphysema, bacterial infections, viral infections, and fungal infections.

3. The method of claim 2 wherein said SP-D protein is administered intratracheally.

4. The method of claim 3 wherein said SP-D protein is introduced by aerosolization.

5. The method of claim 4 wherein said method further comprises administration of IL-4.

6. The method of claim 4 wherein said method further comprises administration of SP-A.

7. The method of claim 4 wherein said method further comprises administration of SP-B.

8. The method of claim 4 wherein said method further comprises administration of SP-C.

9. The method of claim 4 wherein said method further comprises administration of IL-4, SP-A, SP-B, and SP-C.

10. A method for decreasing levels of phosphatidylcholine in the mammalian lung, comprising:
   administering a composition consisting essentially of mammalian surfactant protein-D (SP-D) protein into a human in an amount effective to reduce said pulmonary phosphatidylcholine levels.

11. A method for the treatment of a pulmonary viral disease comprising:
   introducing a composition consisting essentially of mammalian surfactant protein-D (SP-D) into a human in an amount effective to reduce the number of viruses or symptoms of the pulmonary viral disease.

12. The method of claim 11 wherein the pulmonary viral disease is caused by a virus selected from the group consisting of: Adenovirus, Respiratory Syncytial virus (RSV), and Influenza virus.

13. A method for decreasing pulmonary virus titer, comprising:
   introducing a composition consisting essentially of a mammalian surfactant protein-D (SP-D) protein into a human in an amount effective to reduce said pulmonary virus titer.

14. A method of inhibition of metalloproteinase activity and reactive oxygen species in the lungs, comprising:
   administering a composition consisting essentially of surfactant protein-D (SP-D) protein to the lungs in an amount effective to inhibit metalloproteinase activity and reactive oxygen species.

15. A method for the treatment of pulmonary disease comprising: administering a recombinantly expressed mammalian surfactant protein-D (SP-D) protein into a human in an amount effective to reduce the symptoms of pulmonary disease.

16. The method of claim 15 wherein the pulmonary disease is selected from the group consisting of: emphysema, bacterial infections, viral infections, and fungal infections.

17. The method of claim 16 wherein said recombinantly expressed mammalian surfactant protein-D (SP-D) protein is administered intratracheally.

18. The method of claim 17 wherein said recombinantly expressed mammalian surfactant protein-D (SP-D) protein is introduced by aerosolization.

19. The method of claim 18 wherein said method further comprises administration of IL-4.

20. The method of claim 18 wherein said method further comprises administration of SP-A.

21. The method of claim 18 wherein said method further comprises administration of SP-B.

22. The method of claim 18 wherein said method further comprises administration of SP-C.

23. The method of claim 18 wherein said method further comprises administration of IL-4, SP-A, SP-B, and SP-C.

24. A method for decreasing levels of phosphatidylcholine in the mammalian lung, comprising:
   administering a recombinantly expressed mammalian surfactant protein-D (SP-D) protein into a human in an amount effective to reduce said pulmonary phosphatidylcholine levels.

25. A method for the treatment of a pulmonary viral disease comprising:
   administering a recombinantly expressed mammalian surfactant protein-D (SP-D) protein into a human in an amount effective to reduce the number of viruses or symptoms of the viral disease.

26. A method for decreasing pulmonary virus titer, comprising:
   administering a recombinantly expressed mammalian surfactant protein-D (SP-D) protein into a human in an amount effective to reduce said pulmonary virus titer.

27. A method of inhibition of metalloproteinase activity and reactive oxygen species in the lungs, comprising:
   administering a recombinantly expressed mammalian surfactant protein-D (SP-D) protein to the lungs in an amount effective to inhibit metalloproteinase activity and reactive oxygen species.

* * * * *

UNITED STATES PATENT AND TRADEMARK OFFICE
Certificate

Patent No. 6,838,428 B2                                                                                                    Patented: January 4, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jeffrey A. Whitsett, Cincinnati, OH (US); and Thomas R. Korfhagen, Cincinnati, OH (US).

Signed and Sealed this Sixth Day of December 2011.

<div style="text-align: right;">
SUE LIU<br>
<em>Supervisory Patent Examiner</em><br>
Art Unit 1653<br>
Technology Center 1600
</div>

UNITED STATES PATENT AND TRADEMARK OFFICE
CERTIFICATE OF CORRECTION

| | | |
|---|---|---|
| PATENT NO. | : 6,838,428 B2 | Page 1 of 1 |
| APPLICATION NO. | : 09/558576 | |
| DATED | : January 4, 2005 | |
| INVENTOR(S) | : Jeffrey A. Whitsett and Thomas R. Korfhagen | |

It is certified that error appears in the above-identified patent and that said Letters Patent is hereby corrected as shown below:

In Column 1, Lines 10-16, please delete:

"GOVERNMENT INTEREST IN THE INVENTION

Certain aspects of the invention disclosed herein were made with United States government support under National Institutes of Health grants HL 41320, SCOR HL 56387, HL 28623, HL 58795, and HL 03905. The United States government has certain rights in these aspects of the invention."

In Column 1, Lines 10-16, please insert:

--STATEMENT REGARDING FEDERALLY SPONSORED R&D

This invention was made with government support under HL041320, SCOR HL056387, HL028623, HL058795, and HL003905, awarded by the National Institutes of Health. The government has certain rights in the invention.--

Signed and Sealed this
Third Day of January, 2012

David J. Kappos
*Director of the United States Patent and Trademark Office*